United States Patent
Mumm et al.

(10) Patent No.: US 11,413,332 B2
(45) Date of Patent: *Aug. 16, 2022

(54) METHODS OF USING INTERLEUKIN-10 FOR TREATING DISEASES AND DISORDERS

(71) Applicant: Eli Lilly and Company, Indianapolis, IN (US)

(72) Inventors: John Brian Mumm, Los Altos Hills, CA (US); Ivan Ho Chan, Redwood City, CA (US); Martin Oft, Palo Alto, CA (US)

(73) Assignee: ARMO BIOSCIENCES, INC., Redwood City, CA (US)

( * ) Notice: Subject to any disclaimer, the term of this patent is extended or adjusted under 35 U.S.C. 154(b) by 1220 days.

This patent is subject to a terminal disclaimer.

(21) Appl. No.: 15/031,651

(22) PCT Filed: Nov. 7, 2014

(86) PCT No.: PCT/US2014/064620
§ 371 (c)(1),
(2) Date: Apr. 22, 2016

(87) PCT Pub. No.: WO2015/070060
PCT Pub. Date: May 14, 2015

(65) Prior Publication Data
US 2016/0243196 A1    Aug. 25, 2016

Related U.S. Application Data

(60) Provisional application No. 61/902,702, filed on Nov. 11, 2013.

(51) Int. Cl.
| | | |
|---|---|---|
| *A61K 38/20* | (2006.01) | |
| *A61K 45/06* | (2006.01) | |
| *A61K 47/10* | (2017.01) | |
| *A61K 47/60* | (2017.01) | |
| *A61K 9/00* | (2006.01) | |
| *A61K 39/395* | (2006.01) | |

(52) U.S. Cl.
CPC ........ *A61K 38/2066* (2013.01); *A61K 9/0019* (2013.01); *A61K 39/395* (2013.01); *A61K 39/3955* (2013.01); *A61K 45/06* (2013.01); *A61K 47/10* (2013.01); *A61K 47/60* (2017.08)

(58) Field of Classification Search
CPC .......................... A61K 38/2066; A61K 39/395
See application file for complete search history.

(56) References Cited

U.S. PATENT DOCUMENTS

| | | |
|---|---|---|
| 4,965,195 A | 10/1990 | Namen et al. |
| 5,032,396 A | 7/1991 | Williams |
| 5,229,115 A | 7/1993 | Lynch |
| 5,231,012 A | 7/1993 | Mosmann et al. |
| 5,252,714 A | 10/1993 | Harris et al. |
| 5,328,989 A | 7/1994 | Vellekamp et al. |
| 5,552,303 A | 9/1996 | Grabstein et al. |
| 5,624,823 A | 4/1997 | Sachs et al. |
| 5,643,575 A | 7/1997 | Martinez et al. |
| 5,665,345 A | 9/1997 | Yarchoan et al. |
| 5,696,234 A | 12/1997 | Zurawski et al. |
| 5,705,149 A | 1/1998 | Namen et al. |
| 5,710,251 A | 1/1998 | Vellekamp et al. |
| 5,759,859 A | 6/1998 | Leder et al. |
| 5,824,784 A | 10/1998 | Kinstler et al. |
| 5,866,134 A | 2/1999 | Fine et al. |
| 5,876,969 A | 3/1999 | Fleer et al. |
| 5,908,621 A | 6/1999 | Glue et al. |
| 5,919,455 A | 7/1999 | Greenwald et al. |
| 5,932,462 A | 8/1999 | Harris et al. |
| 5,945,097 A | 8/1999 | Cutler et al. |
| 5,951,974 A | 9/1999 | Gilbert et al. |
| 5,985,263 A | 11/1999 | Lee et al. |
| 5,985,265 A | 11/1999 | Kinstler et al. |
| 5,985,857 A | 11/1999 | Kinstler et al. |
| 5,989,867 A | 11/1999 | Knappe et al. |
| 6,156,301 A | 12/2000 | Namen et al. |
| 6,217,857 B1 | 4/2001 | Mosmann et al. |
| 6,387,364 B1 | 5/2002 | Ferguson |
| 6,428,985 B1 | 8/2002 | Bromberg et al. |
| 6,660,258 B1 | 12/2003 | Tovey |
| 6,685,931 B1 | 2/2004 | Grint et al. |
| 6,770,272 B2 | 8/2004 | Strom et al. |
| 6,989,377 B2 | 1/2006 | Hayes et al. |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Teng et al. Stable IL-10: A new therapeutic that promotes tumor immunity. Cancer Cell 20; Dec. 13, 2011 (Year: 2011).*
Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28 (Year: 2002).*
Brown et al. Tolerance to Single, but Not Multiple, Amino Acid Replacements in Antibody VH CDR2. J Immunol. May 1996; 156(9): 3285-91 (Year: 1996).*
Heppner et al. Tumor heterogeneity:biological implications and therapeutic consequence. Cancer Metastasis Review 2:5-23; 1983 (Year: 1983).*
Jain RK. Barriers to drug delivery in solid tumors. Scientific American, Jul. 1994, 58-65 (Year: 1994).*

(Continued)

*Primary Examiner* — Nanessa L. Ford
*Assistant Examiner* — Sandra Dillahunt
(74) *Attorney, Agent, or Firm* — Quarles & Brady LLP

(57) ABSTRACT

Methods of treating subjects having diseases, disorders, or conditions, including cancer and immune- and inflammatory-related disorders, via the administration of IL-10 in combination with one or more additional agents, and methods and models associated therewith, are provided.

20 Claims, No Drawings

Specification includes a Sequence Listing.

(56) References Cited

U.S. PATENT DOCUMENTS

| | | |
|---|---|---|
| 7,052,684 B2 | 5/2006 | Ferguson |
| 7,052,686 B2 | 5/2006 | Lee et al. |
| 7,056,701 B2 | 6/2006 | Fleer et al. |
| 7,261,882 B2 | 8/2007 | Watkins |
| 7,585,947 B2 | 9/2009 | Morre et al. |
| 7,589,179 B2 | 9/2009 | Gillies et al. |
| 7,611,700 B2 | 12/2009 | Gantier et al. |
| 7,650,243 B2 | 1/2010 | Gantier et al. |
| 7,666,400 B2 | 2/2010 | Chang et al. |
| 7,708,985 B2 | 5/2010 | Morre et al. |
| 7,749,490 B2 | 7/2010 | Sommer et al. |
| 7,939,056 B2 | 5/2011 | Horwitz et al. |
| 8,008,449 B2 * | 8/2011 | Korman ............... A61P 7/06 530/388.15 |
| 8,008,499 B2 * | 8/2011 | Habgood ............ C07D 401/04 546/144 |
| 8,044,175 B2 | 10/2011 | Dransfield et al. |
| 8,067,532 B2 | 11/2011 | MacLean |
| 8,287,856 B2 * | 10/2012 | Li ..................... A61K 38/193 424/130.1 |
| 8,580,247 B2 | 11/2013 | Li et al. |
| 8,618,256 B2 | 12/2013 | Cox |
| 9,833,514 B2 * | 12/2017 | Oft ..................... A61P 15/00 |
| 2002/0044921 A1 | 4/2002 | Lee et al. |
| 2003/0012775 A1 | 1/2003 | Brandt et al. |
| 2003/0186386 A1 | 10/2003 | Hansen et al. |
| 2004/0101965 A1 | 5/2004 | Griesenbach et al. |
| 2004/0213795 A1 | 10/2004 | Collins et al. |
| 2005/0008615 A1 | 1/2005 | Bam et al. |
| 2005/0164352 A1 | 7/2005 | Lauder et al. |
| 2005/0260767 A1 | 11/2005 | Clerici et al. |
| 2006/0046961 A1 | 3/2006 | McKay et al. |
| 2006/0078942 A1 | 4/2006 | Liu et al. |
| 2006/0210534 A1 | 9/2006 | Lee et al. |
| 2006/0258607 A1 | 11/2006 | Jarosch et al. |
| 2007/0134197 A1 | 6/2007 | Eichner et al. |
| 2008/0058246 A1 | 3/2008 | Bhaskaran et al. |
| 2008/0069797 A1 | 3/2008 | Roncarolo et al. |
| 2008/0081031 A1 * | 4/2008 | Oft ..................... C07K 16/3023 424/85.2 |
| 2008/0096252 A1 | 4/2008 | Zamost et al. |
| 2009/0028857 A1 | 1/2009 | Li et al. |
| 2009/0035256 A1 | 2/2009 | Sommer et al. |
| 2009/0214463 A1 | 8/2009 | Slobedman et al. |
| 2009/0214471 A1 | 8/2009 | Oft et al. |
| 2009/0311187 A1 | 12/2009 | Berman et al. |
| 2010/0068147 A1 | 3/2010 | Hibberd et al. |
| 2010/0111898 A1 | 5/2010 | Pelura |
| 2010/0129386 A1 | 5/2010 | Elson et al. |
| 2010/0255496 A1 | 10/2010 | Schrader et al. |
| 2010/0266532 A1 | 10/2010 | Ferguson |
| 2010/0285013 A1 | 11/2010 | Li et al. |
| 2010/0297070 A1 | 11/2010 | Dugan et al. |
| 2011/0009589 A1 | 1/2011 | Harris et al. |
| 2011/0064690 A1 | 3/2011 | Lee et al. |
| 2011/0091419 A1 | 4/2011 | Oft et al. |
| 2011/0250163 A1 | 10/2011 | Blaisdell et al. |
| 2011/0275123 A1 | 11/2011 | Paciotti et al. |
| 2011/0305665 A1 | 12/2011 | Lee et al. |
| 2011/0312010 A1 | 12/2011 | Manuilov |
| 2012/0003221 A1 | 1/2012 | McDonagh et al. |
| 2012/0115926 A1 | 5/2012 | Geary et al. |
| 2012/0142033 A1 | 6/2012 | Fujiwara |
| 2012/0213793 A1 | 8/2012 | Huang |
| 2012/0252742 A1 | 10/2012 | Kranz et al. |
| 2012/0270899 A1 | 10/2012 | Bannister et al. |
| 2012/0321617 A1 | 12/2012 | Osterroth et al. |
| 2013/0022600 A1 | 1/2013 | Li et al. |
| 2013/0156774 A1 | 6/2013 | Kuchroo et al. |
| 2014/0199750 A1 | 7/2014 | Weng et al. |
| 2014/0256626 A1 | 9/2014 | Santi et al. |
| 2014/0271684 A1 | 9/2014 | Li et al. |
| 2014/0314795 A1 | 10/2014 | Riddell et al. |
| 2014/0349402 A1 | 11/2014 | Cooper et al. |
| 2015/0038678 A1 | 2/2015 | Eaton et al. |
| 2015/0118244 A1 | 4/2015 | Shahabi et al. |
| 2015/0265705 A1 | 9/2015 | Li et al. |
| 2016/0340406 A1 | 11/2016 | Zhao et al. |
| 2016/0361415 A1 | 12/2016 | Mumm et al. |
| 2016/0375101 A1 | 12/2016 | Oft |

FOREIGN PATENT DOCUMENTS

| | | |
|---|---|---|
| EP | 0251304 | 1/1988 |
| EP | 2066336 | 9/2012 |
| EP | 2537933 | 12/2012 |
| WO | WO 1992012725 | 8/1992 |
| WO | WO 1992012726 | 8/1992 |
| WO | 1994022473 | 3/1994 |
| WO | 199417773 | 8/1994 |
| WO | 1995/03411 | 2/1995 |
| WO | WO 1995/03411 | 2/1995 |
| WO | WO 1995006058 | 3/1995 |
| WO | WO 1995019780 | 7/1995 |
| WO | WO 1996011953 | 4/1996 |
| WO | WO 1997003690 | 2/1997 |
| WO | WO 1999032134 | 7/1999 |
| WO | WO 2001005821 | 1/2001 |
| WO | WO 2001058950 | 8/2001 |
| WO | WO 2002026265 | 4/2002 |
| WO | 2002085300 | 10/2002 |
| WO | WO 2004044006 | 5/2004 |
| WO | WO 2004/056850 | 7/2004 |
| WO | 2004091517 | 10/2004 |
| WO | 2004106486 | 12/2004 |
| WO | 2005033307 | 4/2005 |
| WO | WO 2006/075138 | 7/2006 |
| WO | 2006094530 | 9/2006 |
| WO | WO 2006119170 | 11/2006 |
| WO | WO 2008054585 | 5/2008 |
| WO | 2009014708 | 1/2009 |
| WO | WO 2009/016043 | 2/2009 |
| WO | WO 2009/036568 | 3/2009 |
| WO | 2010022227 | 2/2010 |
| WO | WO 2010/077853 | 7/2010 |
| WO | WO 2011/051489 | 5/2011 |
| WO | 2011159878 | 12/2011 |
| WO | WO 2012/004384 | 1/2012 |
| WO | WO 2012/050923 | 4/2012 |
| WO | WO 2012/050930 | 4/2012 |
| WO | WO 2013/113008 | 8/2013 |
| WO | 2013130913 | 9/2013 |
| WO | 2014172392 | 10/2014 |
| WO | 2014176373 | 10/2014 |
| WO | WO 2014/172392 | 10/2014 |
| WO | 2014204816 | 12/2014 |
| WO | 2015031316 | 3/2015 |
| WO | WO 2015/070060 | 5/2015 |
| WO | 2015153753 | 10/2015 |
| WO | 2015187295 | 12/2015 |
| WO | 2016145388 | 9/2016 |

OTHER PUBLICATIONS

Sporn et al. Chemoprevention of Cancer. Carcinogenesis, 2000;21: 525-530 (Year: 2000).*
Auerbach et al. Angiogenesis assays: problems and pitfalls. Cancer and Metastasis Reviews, 2000, 19: 167-172 (Year: 2000).*
Gura T. Systems for identifying new drugs are often faulty. Science, 1997, 278(5340): 1041-1042 (Year: 1997).*
Hait. Anticancer drug development: the grand challenges. Nature Reviews/Drug Discovery, 2010; 9: 253-254 (Year: 2010).*
Gravanis et al. The changing world of cancer drug development: the regulatory bodies' perspective. Chin Clin Oncol, 2014; 3:1-5 (Year: 2014).*
Topalian et al. Nivolumab in patients with advanced solid tumors: Survival and long-term safety in a phase I trial. Journal of Clinical Oncology 31, No. 15_suppl (May 20, 2013) 3002-3002) (Year: 2002).*
Teng et al. Cancer Cell, 2011; 20:691-693 (Year: 2011).*
Dinant, et al., (2007) "IL-10 attenuates hepatic I/R injury and promotes hepatocyte proliferation", J. Surg. Res., 141:176-182.

(56) References Cited

OTHER PUBLICATIONS

Gotoh, et al., (2012) "A novel anti-inflammatory role for spleen-derived Interleukin-10 in obesity-induced inflammation n white adipose tissue and liver", Diabetes, 61:1994-2003.
Kumagai, et al., (2013) "Effects of Ezetimibe on hypercholesterolemia in the lipid profile in patients with metabolic syndrome", IJC Metabolic and Endocrine, 1:7-12.
Accession NP_036986.2; GI 148747382; Aug. 10, 2014.
Accession NP_776513.1; GI 41386772; Jan. 4, 2015.
Accession NP_001009327.1; GI 57164347; Feb. 13, 2011.
Accession ABY86619.1; GI 166244598 ; Feb. 4, 2008.
Accession AAC23839.1; GI 3242896; Jun. 8, 2000.
"Guidance for Industry Immunogenicity Assessment for Therapeutic Protein Products," (2013) *FDA Guidances*.
"Highlights of Prescribing Information," (1997) *Rituxan*.
Recombinant Human IL-1 0 Protein, CF R&D Systems, accessed Feb. 22, 2016.
Recombinant Mouse IL-1 0 Protein R&D Systems, accessed Feb. 22, 2016.
Agata et al. (1996) "Expression of the PD-1 antigen on the surface of stimulated mouse T and B lymphocytes," *Int Immunol*; 8(5):765-772.
Aggen (2010) "Engineering Human Single-Chain T Cell Receptors," *Dissertation*; http://hdl.handle.net/2142/18585.
Alvarez et al. (2012) "Effects of PEGylation and Immune Complex Formation on the Pharmacokinetics and Biodistribution of Recombinant Interleukin10 in Mice," *Drug Metab Dispos*; 40(2):360-373.
Ansari and Raghava (2010) "Identification of conformational B-cell Epitopes in an antigen from its primary sequence," *Immunome Res*; 6:9pgs.
Ansell et al. (2002) "Phase 1 study of interleukin-12 in combination with rituximab in patients with B-cell non-Hodgkin lymphoma," *Blood*; 99:67-74.
Arakawa and Tsumoto (2003) "The effects of arginine on refolding of aggregated proteins: not facilitate refolding, but suppress aggregation," *Biochemical and Biophysical Research Communications*; 304:148-152.
Armstrong et al. (1996) "Interleukin 10 (IL-10) regulation of tumour necrosis factor cx (TNF-cx) from human alveolar macrophages and peripheral blood monocytes," *Thorax*; 51:143-149.
Asadullah et al. (1999) "Interleukin 10 Treatment of Psoriasis," *Arch Dermatol.* ; 135-187-192.
Asadullah et al. (2003) "Interleukin 10 Therapy—Review of a New Approach," *Pharmacol. Rev.*; 55-241-269.
Bajetta et al. (1998) "Pilot Study of Subcutaneous Recombinant Human Interleukin 12 in Metastatic Melanoma," *Clinical Cancer Research*; 4:75-85.
Banerjee et al. (2012) "Poly(ethylene glycol)-Prodrug Conjugates: Concept, Design, and Applications," *Journal of Drug Delivery*; Article ID 103973:17 pages.
Bea at al. (2011) "Performance Evaluation of a Multiplex Assay for Future Use in Biomarker Discovery Efforts to Predict Body Composition," *Clin Chem Lab Med.*; 49(5):817-824.
Berger et al. (2009) "Safety and immunologic effects of IL-15 administration in nonhuman primates," *Blood*; 114:2417-2426.
Berman et al. (1996) "Systemic administration of cellular IL-10 induces an effective, specific, and long-lived immune response against established tumors in mice," *J Immunol*; 157:231-238.
Bilzer et al. (2006) "Role of Kupffer cells in host defense and liver disease," *Liver International*; 26:1175-1186.
Biswas et al. (2007) "Pathogen_specific CD8 T Cell Responses Are Directly Inhibited by IL-10," *J Immunol.*; 179:4520-4528.
Brady et al. (1994) "Reflections on a peptide," *Nature*; 368:692-693.
Brooks et al. (2008) "IL-10 and PD-L1 operate through distinct pathways to suppress T-cell activity during persistent viral infection," *PNAS*; 105(51):20428-20433.
Burgess (2009) "Refolding Solubilized Inclusion Body Proteins," *Methods in Enzymology*; 463:259-282.

Cai et al. (1999) "IL-10 enhances NK cell proliferation, cytotoxicity and production of IFN-q when combined with IL-18," *Eur. J. Immunol.*; 29:2658-2665.
Caliceti et al. (2012) "Effect of Plasma Membrane Cholesterol Depletion on Glucose Transport Regulation in Leukemia Cells," *PLoS One*; 7:e41246.
Cannistra & Niloff (1996) "Cancer of the uterine cervix," *New Eng I J Med* 334:1030-1038.
Cao et al. (2011) "Janus kinase activation by cytokine oncostatin M decreases PCSK9 expression in liver cells," *J Lipid Res.*; 52(3):513-530.
Capitini et al. (2009) "Modulating T cell Homeostasis with IL-7: Preclinical and Clinical Studies," *J Intern Med*; 266(2):141-153.
Cebon et al. (2003) "Two phase I studies of low dose recombinant human IL-12 with Melan-A and influenza peptides in subjects with advanced malignant melanoma," *Cancer Immunity*; 3:7 (18 pages).
Chamow et al. (1994) "Modification of CD4 Immunoadhesin with Monomethoxypoly(ethylene glycol) Aldehyde via Reductive Alkylation," *Bioconjugate Chem.*; 5:133-140.
Chan et al. (2015) "The Potentiation of IFN-γ and Induction of Cytotoxic Proteins by Pegylated IL-10 in Human CD8 T Cells," *J Interferon Cytokine Res*; 35(12):948-955.
Chen & Zlotnik (1991) "IL-10: a novel cytotoxic T cell differentiation factor," *J Immunol*; 147:528-534.
Chen et al. (2007) "Prediction of linear B-cell epitopes using amino acid pair antigenicity scale," *Amino Acids*; 33:423-428.
Choi et al. (2006) "Serum adiponectin, interleukin-10 levels and inflammatory markers in the metabolic 1-18 syndrome," *Diabetes Research and Clinical Practice*; 75:235-240.
Collins et al. (2012) "Trastuzumab induces antibody-dependent cell mediated cytotoxicity (ADCC) in HER-2-non-amplified breast cancer cell lines," *Annals of Oncology*; 23:1788-1795.
Compton et al. (2004) "Pathogenesis of Enterotropic Mouse Hepatitis Virus in Immunocompetent and Immunodeficient Mice," *Comparative Medicine*; 54(6):681-689.
Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.
Couder et al. (1993) "Synthesis and biological activities of ψ(CH2NH) pseudopeptide analogues of the C-terminal hexapeptide of neurotensin," *Int. J. Peptide Protein Res.*; 41:181-184.
D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med*; 178:1041-1048.
Das et al. (2012) "IL-10-Producing Regulatory B Cells in the Pathogenesis of Chronic Hepatitis B Virus Infection," *J. Immunol.*; 189(8):3925-3935.
Davidson & Diamond (2001) "Autoimmune diseases," *New Engl J Med*; 345:340-350.
De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med*; 174(4):915-924.
De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.
Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.
Dolgin (2011) "Trial puts niacin—and cholesterol dogma—in the line of fire," *Nature Medicine*; 17(7):356.
Dorner et al. (2011) "A genetically humanized mouse model for hepatitis C virus infection," *Nature*; 474:208-211.
Easy Surf. Blood Volume Calculator [online]Oct. 1, 2012 [retrieved Aug. 18, 2014]. Available on the internet: <URL: https://web.archive.org/web/20121001142649/http://www.easysurf.cc/cnver22.htm >.

(56) References Cited

OTHER PUBLICATIONS

Ehrlich et al. (2013) "Preparation and Characterization of Albumin Conjugates of a Truncated Peptide YY Analogue for Half-Life Extension," *Bioconjug. Chem.*; 24(12):2015-2024.

El-Manzalawy et al. (2008) "Predicting linear B-cell epitopes using string kernels," *J Mol Recognit*; 21:243-255.

Emmerich et al. (2012) "IL-10 directly activates and expands tumor-resident CD8(+) T cells without de novo infiltration from secondary lymphoid organs," *Cancer Res*; 72(14):3570-3581.

Engel et al. (2006) "Using Endoproteinases Asp-N and Glu-C to Improve Protein Characterization," *Promega Corporation*; 10th edition.

Enzinger & Mayer (2003) "Esophageal cancer," *New Eng I J Med*; 349:2241-2252.

Fahnert et al. (2012) "Using Folding Promoting Agents in Recombinant Protein Production: A Review," *Methods inn Molecular Biology*; 824:3-36.

Fang et al. (2015) "Programmed Death 1 (PD-1) is involved in the development of proliferative diabetic retinopathy by mediating activation-induced apoptosis," *Mol Vis*; 21:901-910.

Farrar et al. (1999) "Cancer dormancy. VII. A regulatory role for COB+ T cells and IFN-gamma in establishing and maintaining the tumor-dormant state," *J Imunol* 162:2842-2849.

Fehniger and Caligiuri (2001) "Interleukin 15: biology and relevance to human disease," *Blood*; 97:14-32.

Feingold et al. (1996) "Endotoxin, TNF, and IL-I decrease cholesterol 7a-hydroxylase mRNA levels and activity," *Journ of Lipid Res*; 37:223-228.

Fiorentino et al. (1989) "Two types of mouse T helper cell. IV. Th2 clones secrete a factor that inhibits cytokine production by Th1 clones," J Exp Med; 170:2081-2095.

Forastiere et al. (2001) "Head and neck cancer," *New Engl J Med* 345:1890-1900.

Fridman et al. (2012) "The immune contexture in human tumours: impact on clinical outcome," *Nature*; 12:298-306.

Fry and MacKall (2002) "Interleukin-7: from bench to clinic," *Blood*; 99:3892-3904.

Fujiwara et al. (2010) "Extraction and purification of human interleukin-10 from transgenic rice seeds," *Protein Expression and Purification*; 72:125-130.

Galon et al. (2013) "The Continuum of Cancer Immunosurveillance: Prognostic, Predictive, and Mechanistic Signatures," *Immunity*; 39:11-26.

Gameren et al. (1994) "Effects of Recombinant human interleukin-6 in cancer patients: a phase I-II study," *Blood*; 84:1434-1441.

Gao et al. (2012) "Best: Improved Prediction of B-Cell Epitopes from Antigen Sequences," *PLoS ONE*; 7(6): e40104.

Gargett et al.: 11 Different cytokine and stimulation conditions influence the expansion and immune phenotype of third-generation chimeric antigen receptor T cells specific for tumor antigen GD2, Cytotherapy, vol. 17, No. 4, Apr. 2015 (Apr. 2015), pp. 487-495.

GenBank Accession No. M37897 "Mouse interleukin 10 mRNA, complete cds," dated Apr. 27, 1993.

GenBank Accession No. NP 000563 "interleukin-10 precursor [*Homo sapiens*]," dated Mar. 3, 1995.

Georgescu et al. (1997) "Interleukin-10 Promotes Activation-induced Cell Death of SLE Lymphocytes Mediated by Fas Ligand," *J. Clin. Invest.*; 100:2622-2633.

Gerstein et al. (2008) "Effects of Intensive Glucose Lowering in Type 2 Diabetes," *New England J of Medicine*; 358(24):2545-2559.

Gesser et al. (1997) "Identification of functional domains on human interleukin 10," *Proc. Natl. Acad. Sci.*; 94:14620-14625.

Gierens et al. (2000) "Interleukin-6 Stimulates LDL Receptor Gene Expression via Activation of Sterol-Responsive and Sp1 Binding Elements," *Arterioscler Thromb Vase Biol.* ; 20:1777-1783.

Gill et al., (2015) "Going viral: Chimeric antigen receptor T-cell therapy for hematological malignancies", Immunological Reviews 28150181 Blackwell Publishing Ltd GBR, vol. 263, No. 1, pp. 68-89.

Gregoriadis et al., (2005) "Improving the therapeutic efficacy of peptides and proteins: A role for polysialic acids," *Int. J. Pharmaceutics*; 300(1-2):125-130.

Groux et al. (1998) "A transgenic model to analyze the immunoregulatory role of IL-10 secreted by antigen-presenting cells," *J Immunol*; 162:1723-1729.

Groux et al. (1998) "Inhibitory and stimulatory effects of IL-10 on human COB+ T cells," *J Immunol*; 160:3188-3193.

Hagenbaugh et al. (1997) "Altered immune responses in interleukin 10 transgenic mice," *J Exp Med*; 185:2101-2110.

Hamada et al. (2009) "Effect of Additives on Protein Aggregation," *Current Pharm Biotech*; 10:400-407.

Hashizume et al. (2010) "Overproduced interleukin 6 decreases blood lipid levels via upregulation of very-low-density lipoprotein receptor," *Ann Rheum Dis*; 69:741-746.

Heeschen et al. (2003) "Serum Level of the Antiinflammatory Cytokine Interleukin-1 0 Is an Important Prognostic Determinant in Patients With Acute Coronary Syndromes," *Circulation*; 107:2109-2114.

Hombach et al. (2013) "Arming Cytokine-induced Killer Cells With Chimeric Antigen Receptors: CD28 Outperforms Combined CD28-OX40 'Super-stimulation'," *Molecular Therapy*; 12:2268-2277.

Howard et al. (1993) "Interleukin 10 Protects Mice from Lethal Endotoxemia," *J. Exp. Med.*; 177:1205-1208.

Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.

Huang et al. (2010) "Depletion of Liver Kupffer Cells Prevents the Development of Diet-Induced Hepatic Steatosis and Insulin Resistance," 59:347-357.

Huntington et al. (2008) "IL-15 trans-presentation promotes human NK cell development and differentiation in vivo," *J. Exp. Med.*; 206:25-34.

Hustoft et al. (2012) "A Critical Review of Trypsin Digestion for LC-MS Based Proteomics," *InTech*; Chapter 4.

Infante et al. (2015) "A first-in-human dose escalation study of PEGylated recombinant human IL-10 (AM0010) in advanced solid tumors," *ASCO Meeting Abstracts*; 33(15 suppl):3017.

International Search Report; PCT/US01/42431, dated. Aug. 20, 2002.

Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.

Izbicki et al. (1997) "Prognostic value of immunohistochemically identifiable tumor cells in lymph nodes of patients with completely resected esophageal cancer," *New Engl J Med*; 337:1188-1194.

Jameson et al. (1994) "A rationally designed CD4 analogue inhibits experimental allergic encephalomyelitis," *Nature*; 368:744-746.

Jevševar et al. (2010) "PEGylation of therapeutic proteins," *Biotechnol. J.*; 5:113-128.

Jiang et al. (2015) "T-cell exhaustion in the tumor microenvironment," *Cell Death Dis*;6:e1792.

Josephson et al. (2001) "Crystal Structure of the IL-10/IL-10R1 Complex Reveals A Shared Receptor Binding Site," *Immunity*; 14:35-46.

Jungbauer et al. (2007) "Current status of Technical protein refolding," *Journal of Biotechnology*; 128:587-596.

Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.

Khow and Suntrarachun (2012) "Strategies for production of active eukaryotic proteins in bacterial expression system," *Asian Pac. J. Biomed.*; 2(2):159-162.

Kimball et al. (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.

Kinstler et al. (1996) "Characterization and Stability of N-terminally PEGylated rhG-CSF," *Pharm. Res.*; 13:996-1002.

(56) References Cited

OTHER PUBLICATIONS

Kinstler et al. (2002) "Mono-N-terminal poly(ethylene glycol)-protein conjugates," *Advanced Drug Delivery Reviews*; 54:477-485.

Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.

Kokura et al. (2003) "The blocking of NFkB activation by systemicinterleukin-10 gene therapy inhibits liver and lung metastasis of colon 26 adenocarcinoma in mice" *Gastroenterology*; 124(4): Abstract No. W965.

Kokura et al. (2005) "Interleukin-1 0 plasmid DNA inhibits subcutaneous tumor growth of Colon adenocarcinoma in mice," *Cancer Letters*; 218:171-179.

Kong et al. (2005) "In vivo activities of cytokine oncostatin M in the regulation of plasma lipid levels," *Journal of Lipid Research*; 46:1163-1171.

Körholz et al. (1997) "The Role of Interleukin-10 (IL-10) in IL-15—Mediated T-Cell Responses," *Blood*; 90(11):4513-4521.

Kundu et al. (1996) "Antimetastatic and antitumor activities of interleukin 10 in a murine model of breast cancer," *J Nail Cancer Inst*; 88:536-541.

Kundu et al. (1997) "Interleukin-10 inhibits tumor metastasis, down regulates MHC class I, enhances NK lysis," *Cellular Immunology, Academic Press*; 180(1):55-61.

Kute et al. (2012) "Understanding key assay parameters that affect measurements of trastuzumab-mediated ADCC against Her2 positive breast cancer cells," *OncoImmunology*; 1(6):810-821.

Langowski et al. (2006) "IL-23 promotes tumour incidence and growth," *Nature*; 442:461-465.

Lasek et al. (2014) "Interleukin 12: still a promising candidate for tumor immunotherapy?" *Cancer Immunol Immunother*; 63:419-435.

Le et al. (2001) "Pre-existing tumor-sensitized T cells are essential for eradication of established tumors by IL-12 and cyclophosphamide plus IL-12," *J Immunol*; 167:6765-6772.

Lehmann et al. (2014) "IL-12 Directs Further Maturation of Ex Vivo Differentiated NK Cells with Improved Therapeutic Potential," *PLoS One*; 9(1):e87131 (12 pages).

Lewington and Clark (2005) "Combined Effects of Systolic Blood Pressure and Total Cholesterol on Cardiovascular Disease Risk," *Circulation*; 112:3373-3374.

Lindhout et al. (2011) "Site-specific enzymatic polysialylation of therapeutic proteins using bacterial enzymes," *PNAS*; 108(18)7397-7402.

Liu et al. (2003) "IL-10 Mediates Suppression of the CD8 T Cell IFN-γ Response to a Novel Viral Epitope in a Primed Host," *J Immunol*; 171:4765-4772.

Loebbermann et al. (2012) "IL-10 Regulates Viral Lung Immunopathology during Acute Respiratory Syncytial Virus Infection in Mice," *PLoS ONE*; 7(2):e32371.

Lopez et al. (2005) "IL-12 and IL-10 Expression Synergize to Induce the Immune-Mediated Eradication of Established Colon and Mammary Tumors and Lung Metastasis," *J Immunol*; 175:5885-5894.

Lowe et al. (1998) "Impact of Major Cardiovascular Disease Risk Factors, Particularly in Combination, on 22-Year Mortality in Women and Men," *Arch Intern Med*; 158:2007-2014.

Lu et al. (2004) "Prognostic factors in resected stage I non-small-cell lung cancer: a multivariate analysis of six molecular markers," *J Clin Oneal*; 22:4575-4583.

Lugli et al. (2010) "Transient and persistent effects of IL-15 on lymphocyte homeostasis in nonhuman primates," *Blood*; 116:3238-3248.

Lynch and Chapelle (2003) "Hereditary colorectal cancer," *New Eng I J Med*; 348:919-932.

Martin et al. (2001) "B-Cell Deficiency Suppresses Vaccine-Induced Protection against Murine Filariasis but Does not Increase the Recovery Rate for Primary Infection," *Infect. Immun.*; 69(11)7067-7073.

Mattos et al. (2012) "PEGylation of interleukin-10 improves the pharmacokinetic profile and enhances the antifibrotic effectivity in CCI.-induced fibrogenesis in mice," *J Control Release*; 162(1):84-91.

Maus et al. (2014) "Antibody-modified T cells: CARs take the front seat for hematologic malignancies," *Blood*; 123(17):2625-2635.

Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.

Monk (2011) "A Strategy for the Quantification of Protein Polyethylene Glycol (PEG) Derivatized Sites using iTRAQ," *University of California, San Diego*; 1-51.

Moore et al. (1990) "Homology of cytokine synthesis inhibitory factor (IL-10) to the Epstein-Barr virus gene BCRFI," *Science*; 248:1230-1234.

Moran et al. (1994) "Human leukemia inhibitory factor inhibits development of experimental atherosclerosis," *Arterioscler Thromb Vase Biol.*; 14(8):1356-1363.

Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.

Mumm et al. (2011) "IL-10 elicits IFNγ-dependent tumor immune surveillance," *Cancer Cell*; 20(6):781-796.

Naicker et al. (2009) "Interleukin-10 Promoter Polymorphisms Influence HIV-1 Susceptibility and Primary HIV-1 Pathogenesis," *J. Infect. Dis.*; 200(3):448-452.

Natsume et al. (2009) "Improving effector functions of antibodies for cancer treatment: Enhancing ADCC and CDC," *Drug Design, Development and Therapy*; 3:7-16.

Nenseter et al. (1992) "Role of liver endothelial and Kupffer cells in clearing low density lipoprotein from blood in hypercholesterolemic rabbits," *J of Lipid Res*; 33:867-877.

Neven et al. (2013) "A Mendelian predisposition to B cell lymphoma caused by IL-10R deficiency," *Blood*; 122(23):3712-3722.

Neyrinck et al. (2009) "Critical role of Kupffer cells in the management of diet-induced diabetes and obesity," *Biochemical and Biophysical Research Communications*; 385:351-356.

Nicholls et al. (2012) "Is niacin ineffective? Or did AIM-HIGH miss its target?," *Cleveland Clinic Journ of Med*; 79(1):38-43.

Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.

Osaki et al. (1999) "Potent antitumor effects mediated by local expression of the mature form of the interferon-γ inducing factor, interleukin-18 (IL-18)," *Gene Therapy*; 6:808-815.

Osborne (1998) "Tamoxifen in the treatment of breast cancer," *New Engl J Med*; 339:1609-1618.

Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology*; 187:3383-3390.

Pardoll (2012) "The blockade of immune checkpoints in cancer immunotherapy," *Cancer*; 12:252-264.

Park et al. (2011) "IL-15-lnduced IL-10 Increases the Cytolytic Activity of Human Natural Killer Cells," *Mol. Cells*; 32:265-272.

Pasut and Veronese (2012) "State of the art in PEGylation: The great versatility achieved after forty years of research," *Journal of Controlled Release*; 161:461-472.

Payne et al. (2010) "Product development issues for PEGylated proteins," *Pharmaceutical Development and Technology*; 16:423-440.

Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.

(56) References Cited

OTHER PUBLICATIONS

Pellegrini et al. (2011) "IL-7 Engages Multiple Mechanisms to Overcome Chronic Viral Infection and Limit Organ Pathology," *Cell*; 144:1-13.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.
Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.
Rachmawati et al. (2007) "Chemical Modification of Interleukin-10 with Mannose 6-Phosphate Groups Yields a Liver-Selective Cytokine," *Drug Metabolism and Disposition*; 35(5):814-821.
Radwanski et al. (1998) "Pharmacokinetics and Leukocyte Responses of Recombinant Human Interleukin-10," *Pharm. Res.*; 15(12):1895-1901.
Ramirez-Montagut et al. (2003) "Immunity to melanoma: unraveling the relation oftumor immunity and autoimmunity," *Oncogene*; 22:3180-3187.
Re et al. (2002) "Preclinical evaluation of the antiproliferative potential of STI571 in Hodgkin's disease," *British Journal of Cancer*; 86:1333-1335.
Reynolds, et al. (2002) "Proteolytic 180 Labeling for Comparative Proteomics: Evaluation of Endoprotease Glu-C as the Catalytic Agent," *Journal of Proteome Research*; 1 (1):27-33.
Roberts et al. (2012) "Chemistry for peptide and protein PEGylation," *Advanced Drug Delivery Reviews*; 64:116-127.
Rolfe et al. (2003) "Leukemia inhibitory factor retards the progression of atherosclerosis," *Cardiovascular Research*; 58:222-230.
Russo et al. (2006) "Randomized trial of pegylated interferon a-2b monotherapy in haemodialysis patients with chronic hepatitis C," *Nephrol Dial Transplant*; 21:437-443.
Saha and Raghava (2006) "Prediction of continuous B-cell epitopes in an antigen using recurrent neural network," *Proteins*; 65:40-48.
Sakamoto et al. (2003) "Interleukin-10 gene therapy enhances antitumor effect of CPT-11 for lung metastasis of colon26 adenocarcinoma in mice," *Gastroenterology*; 124(4):A456-A457.
Sawaya et al. (2003) "Risk of cervical cancer associated with extending the interval between cervical-cancer screenings," *New Engl J Med*; 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.
Sela and Zisman (1997) "Different roles of D-amino acids in immune phenomena," *Faseb J.*; 11:449-456.
Shen et al. (2013) "Proprotein convertase subtilisin/kexin type 9 potentially influences cholesterol uptake in macrophages and reverse cholesterol transport," *FEBS Letters*; 587:1271-1274.
Smith et al. (1996) "Administration of interleukin-1 0 at the time of priming protects Corynebacterium parvum-primed mice against LPS- and TNF-alpha-induced lethality," *Cellular Immunology* 173(2):207-214.
Sneller et al. (2011) "IL-15 administered by continuous infusion to rhesus macaques induces massive expansion of CD8 T effector memory population in peripheral blood," *Blood*; 118(26):6845-6848.
Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.
Song et al. (2012) "CD27 costimulation augments the survival and antitumor activity of redirected human T cells in vivo," *Blood*; 119(3):696-706.
Srivastava et al. (2013) "Effects of interleukin-18 on natural killer cells: costimulation of activation through Fc receptors for immunoglobulin," *Cancer Immunol Immunother*; 62(6):1073-1082.
Storici and Resnick (2006) "The delitto perfetto approach to in vivo site-directed mutagenesis and chromosome rearrangements with synthetic oligonucleotides in yeast," *Methods in Enzymology*; 409:329-345.
Sweredoski and Baldi (2009) "COBEpro: a novel system for predicting continuous B-cell epitopes," *Protein Eng Des Sel*; 22:113-120.
Syto et al. (1998) "Structural and biological stability of the human interleukin 10 homodimer," *Biochemistry*; 37(48):16943-16951.
Teng et al. (2015) "IL-12 and IL-23 cytokines: from discovery to targeted therapies for immune-mediated inflammatory diseases," *Nature Medicine*; 21:719-729.
Teng et al.: "Stable IL-10: A new therapeutic that promotes tumor immunity" Cancer Cell 2011 Cell Press USA, vol. 20, No. 6, Dec. 13, 2011 (Dec. 13, 2011), pp. 691-693.
Tilg et al. (2002) "Treatment of Crohn's disease with recombinant human interleukin 10 induces the proinflammatory cytokine interferon γ," *Gut*; 50:191-195.
Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.
Trehin et al. (2004) "Cellular uptake but low permeation of human calcitonin-derived cell penetrating peptides and Tat(47-57) through well-differentiated epithelial models," *Pharm. Research*; 21:1248-1256.
Tsumoto et al. (2003) "Practical considerations in refolding proteins from inclusion bodies," *Protein Expression and Purification*; 28:1-8.
Tsumoto et al. (2004) "Role of Arginine in Protein Refolding, Solubilization, and Purification," *Biotechnol. Prog.*; 20:1301-1308.
Valabrega et al. (2007) "Trastuzumab: mechanism of action, resistance and future perspectives in HER2-overexpressing breast cancer," *Annals of Oncology*; 18:977-984.
Van Deventer et al. (1997) "Multiple Doses of Intravenous Interleukin 10 in Steroid-Refractory Crohn's Disease," *Gastroenterology*, 113:383-389.
Vicari and Trinchieri (2004) "Interleukin-10 in viral diseases and cancer: exiting the labyrinth?," *Immunological Reviews*; 202:223-236.
Vigneron et al. (2013) "Database of T cell-defined human tumor antigens: the 2013 update," *Cancer Immunity*; 13:15-20.
Virgin, et al. (2009) "Redefining Chronic Viral Infection," *Cell*; 138:30-50.
Von Andrian and Mackay (2000) "T-cell function and migration. Two sides of the same coin," *New Engl J Med*; 343:1020-1034.
Waldmann et al. (2011) "Safety (toxicity), pharmacokinetics, immunogenicity, and impact on elements of the normal immune system of recombinant human IL-15 in rhesus macaques," *Blood*; 117:4787-4795.
Walter and Nagabhushan (1995) "Crystal structure of interleukin 10 reveals an interferon gamma-like fold," *Biochemistry*; (38):12118-12125.
Wee et al. (2010) "SVM-based prediction of linear B-cell epitopes using Bayes Feature Extraction," *BMC Genomics*; 11 (Supp 4):S21.
Wender et al. (2000) "The design, synthesis, and evaluation of molecules that enable or enhance cellular uptake: peptoid molecular transporters," *Proc. Natl. Acad. Sci. USA*; 97:13003-13008.
Wilson et al. (2011) "The role of IL-10 in regulating immunity to persistent viral infections," *Curr Top Microbiol Immunol.*; 350: 39-65.
Witsch et al. (2010) "Roles for Growth Facotes in Cancer Progression," *Physiology*; 25(2):85-101.
Wu et al. (2012) "Immunotherapies: The Blockade of Inhibitory Signals," *Int. J. Biol. Sci.*; 8:1420-1430.
Xu et al. (2010) "Regulation of Antitumor Immune Responses by the IL-12 Family Cytokines, IL-12, IL-23, and IL-27," *Clinical and Developmental Immunology*; Article ID:832454 (9 pages).
Yamaguchi and Miyazaki (2014) "Refolding Techniques for Recovering Biologically Active Recombinant Proteins from Inclusion Bodies," *Biomolecules*; 4:235-251.
Yoshioka et al. (2011) "Development of a novel DDS for site-specific PEGylated proteins," *Chem. Central J.*; 5:25.

(56) References Cited

OTHER PUBLICATIONS

Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.

Zauner et al. (1996) "Glycerol Enhancement of Ligand-Polylysine/DNA Transfection," *BioTechniques*; 20:905-913.

Zdanov et al. (1995) "Crystal structure of interleukin-10 reveals the functional dimer with an unexpected topological similarity to interferon γ," *Structure*; 3:591-601.

Zdanov et al. (1996) "Crystal structure of human interleukin-10 at 1.6 A resolution and a model of a complex with its soluble receptor," *Protein Sci.*; (10):1955-1962.

Zender et al. (2002) "VP22-mediated intercellular transport of p53 in hepatoma cells in vitro and in vivo," *Cancer Gene Ther.*; 9(6):489-496.

Zheng et al. (1996) "Interleukin-10 inhibits tumor metastasis through an NK celldependent mechanism," *J Exp Med*; 184:579-584.

Shang, et al., (2017) "CARs: Synthetic immunoreceptors for cancer therapy and beyond", Trends Mol. Med., 23:430-450.

Hermanson, et al., (2015) "Utilizing chimeric antigen receptors to direct natural killer cell activity", Frontiers in Immunology, 6:195.

Jaspers, et al., (2017) "Development of CART cells designed to improve antitumor efficacy and safety", Pharmac. & Therap., http://dx.doi.org,/1 0.1 016/j.pharmthera.2017.03.012.

Jensen, et al., (2015) "Designing chimeric antigen receptors to effectively and safely target tumors", Curr. Opin. Immunol., 33:9-15.

Chmielewski, et al., (2015) "TRUCKs: the fourth generation of CARs", Exp. Opin. Bioi. Ther., 15:1145-1154.

Hombach, et al., (2012) "OX40 costimulation by a chimeric antigen receptor abrogates CD28 and IL-2 induced IL-10 secretion by redirected CD4+ T cells", Oncolmmunol., 1:458-466.

Newick, et al., (2016) "CART cell therapy for solid tumors", Annu. Rev. Med., 68:139-152.

Gill, et al., (2015) "Going Viral: chimeric antigen receptor T-cell therapy for hematological malignancies", Immunol. Rev., 263:68-89.

Muecke, Susanne, et al., (2000) "Suppression of the Tumorigenic Growth of Burkitt's Lymphoma Dells in Immunodeficient Mice by Cytokine Gene Transfer Using EBV-Derived Episomal Expression Vectors", Int. J. Cancer, 86:301-306.

Mumm, John B., et al., (2012) "Killing from within" Oncolmmunology, 1(9): 1598-1600.

Klebanoff, CA et al., (2004) "IL-15 Enhances the in vivo Antitumor Activity of Tumor-reactive CD8+ T Cells", Proceedings of the National Academy of the Sciences of the U.S.A., 101(7):1969-1974.

Steel, JC et al., (2012) "Biology and its Therapeutic Implications in Cancer", Trends in Pharmacological Sciences, 33(1):35-41.

Wylie, Davie, C., et al.; (2001) "Carboxyalkylated Histidine Is a pH-Dependent Product of Pegylation with SC-PEG", Pharmaceutical Research, 18(9):2-8.

PeproTech, "Recombinant Human IL-10 (carrier-free)", (2017) 7 pages.

Biolegend, "Recombinant Human IL-10 (carrier-free)", (2007) 3 pages.

Anstee and Goldin, (2006) "Mouse models in non-alcoholic fatty liver disease and steatohepatitis research", Int. J. Exp. Path., 87:1-16.

Cosma, Meda, (2014) :The impact of cytokines and chemokines on non-alcoholic fatty liver disease (NAFLD), Biotechnology, Molecular Biology and Nanomedicine, 2(1):15-16.

Gotoh, Koro, et al., (2017) "Role of spleen-derived IL-10 in prevention of systemic low-grade inflammation by obesity", Endocrine Journal, 64(4):375-378.

Gotoh, Koro, (2012) "Spleen-Derived Interleukin-10 Downregulates the Severity of High-Fat Diet-Induced Non-Alcoholic Fatty Pancreas Disease", PLOS, 12 pages.

Larter and Yeh, (2008) "Animal models of NASH: Getting both pathology and metabolic context right", Journal of Gastroenterology and Hepatology, 23:1635-1648.

Lauw, Fanny, et al., (2000) "Proinflammatory Effects of IL-10 During Human Endotoxemia", J Immunol, 165:2783-2789.

Millic, Sandra, et al., (2014) "Non-alcoholic fatty liver disease and obesity: Biochemical, metabolic and clinical presentations". World J Gastroenterol, 20(28):9330-9337.

Neyrinck, Audrey, et al., (2002) "Inhibition of Kupffer cell activity induces hepatic triglyceride synthesis in fasted rats, independent of lipopolysaccharide challenge", Journal of Hepatology, 36:466-473.

Rachmawati, Heni, et al., (2004) "Pharmacokinetic and Biodistribution Profile of Recombinant Human Interleukin-10 Following Intravenous Administration in Rats with Extensive Liver Fibrosis", Pharmaceutical Research, 21 (11):2072-2073.

Wan, Jinghong, et al., (2014) "M2 Kupffer Cells Promote M1 Kupffer Cell Apoptosis: A Protective Mechanism Against Alcoholic and Nonalcoholic Fatty Liver Disease", Hepatology, 59(1):131-142.

Liang, et al., (2014) "Establishment of a General NAFLD Scoring System for Rodent Models and Comparison to Human Liver Pathology", PLOSone, 17 pages.

Spoto, et al., (2013) "Spleen IL-10, A Key Player in Obesity-Driven Renal Risk", Nephrol Dial Transplant, 28:1061-1064.

Liedtke, et al., (2013) "Experimental liver fibrosis research: update on animal models, legal issues and translational aspects", Fibrogenesis Tissue Repair, 6(19):1-25.

Paulsen and Reichelt, (1992) "Mouse liver regeneration after carbon tetrachloride injury as test system for hepatic growth regulators" Virchows Archiv B Cell Pathol, 62:173-177.

Bieghs, et al., (2012) "LDL Receptor Knock-Out Mice Are a Physiological Model Particularly Vulnerable to Study the Onset of Inflammation in Non-Alcoholic Fatty Liver Disease", PLoS ONE, 7(1):1-11.

Scotton and Chambers, (2010) "Bleomycin revisited: towards a more representative model of IPF?", Am J Physiol Lung Cell Mol Physiol, 299:L439-L441.

Abbasi, Amanullah, et al., (2012) "Serum Cholesterol: Could it be a Sixth Parameter of Child-Pugh Scoring System in Cirrhotics Due to Viral Hepatitis?", Journal of the College of Physicians and Surgeons Pakistan, 22(8):484-487.

Nelson, David R., (2003) "Long-Term Interleukin 10 Therapy in Chronic Hepatitis C Patients Has a Proviral and Anti-inflammatory Effect", Hepatology, 38(4):859-868.

Woodhouse, Stephen D., et al., (2010) "Transcriptome Sequencing, Microarray, and Proteomic Analyses Reveal Cellular and Metabolic Impact of Hepatitis C Virus Infection InVitro", Hepatology, 52(2):443-453.

Mattos, Adriana, et al., (2012) "PEGylation of interleukin-10 improves the pharmacokinetic profile and enhances the antifibrotic effectivity in CCI4 induced fibrogenesis in mice", Journal of Controlled Release, 162:84-91.

Virkkunen, M., (1979) "Serum Cholesterol in Antisocial Personality", Neuropsychobiology, 5:27-30.

Pjrek, Edda, et al., (2007) "Serum lipid levels in seasonal affective disorder", Eur Arch Psychiatry Clin Neurosci, 257:197-202.

Gabriel, A., (2007) "Changes in plasma cholesterol in mood disorder patients: Does treatment make a difference?", Journal of Affective Disorders, 99:273-278.

Papadopoulou, Athanassia, et al., (2013) "Plasma total cholesterol in psychiatric patients after a suicide attempt and in follow-up". Journal of Affective Disorders, 148:440-443.

NCT01025297, (2012) ""Dose Escalation Study of lnterleukin7(IL7) and Bitherapy in HCV Genotype 1 or 4 Patients Resistant to Bitherapy Alone (Eclipse 2)"", Clinical Trials, 6 pages.

Fry and Mackall (2005) ""The Many Faces of IL-7: From Lymphopoiesis toPeripheral T Cell Maintenance"", the Journal of Immunology, 174:6571-6576.

Alpdogan, et al., (2005) "IL-7 and IL-15: therapeutic cytokines for immunodeficiency", Cell, 26(1):56-64.

Stoklasek, et al., (2006) "Combined IL-15/IL-15Ra Immunotherapy Maximizes IL-15 Activity In Vivo", J Immunol, 177(9):6072-6080.

Storek, et al., (2003) ""Interleukin-7 improves CD4 T-cell reconstitution after autologous CD34 celltransplantation in monkeys"", Blood, 101(10):4209-4218.

(56) References Cited

OTHER PUBLICATIONS

Aukrust et al., (2005) "Potential role for immunomodulatory therapy in atherosclerotic plaque stabilization", Expert Opinion Pharmacother, 6:2169-2180.

Cheon, H.G. (2013) "Latest research and development trends in non insulin anti-diabetics", Arch. Pharm. Res., 36:145-153.

Fichtlscherer et al., (2004) "Interieukin-10 serum levels and systemic endothelial vasoreactivity in patients with coronary artery desease", J. Am. Coll. Cardiol., 44:44-49.

Bowie, James, U., et al. (1990) "Deciphering the Message in Protein Sequences: Tolerance to Amino Acid Substitutions", Science, 247:1306-1310.

Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.

Bork, Peer, (2000) "Powers and Pitfalls in Sequence Analysis: The 70% Hurdle", Genome Research, 10:398-400.

Lazar, Eliane, et al. (1988) "Transforming Growth Factor alpha: Mutation of Aspartic Acid 47 and Leucine 48 Results in Different Biological Activities", Mol. Cell. Bioi., 8:1247-1252.

UniProt reference P79338 (1L 1 O_MACFA) (downloaded from http://www.uniprot.org/uniprot/P79338, last sequence update May 1, 1997).

UniProt reference A2T6Z6 (1L 1 O_PANTR) (downloaded from http://www.uniprot.org/uniprot!A2T6Z6, last sequence update Mar. 6, 2007).

Soderquist, et al. (2010) "PEGylation of interleukin-1 0 for the mitigation of enhanced pain states", J Biomed Mater Res A, 3(93):1169-1179.

Tilg, et al., "Induction of circulating interleukin 10 by interleukin 1 and interleukin 2, but not interleukin 6 immunotherapy," *Cytokine*, vol. 7, No. 7, pp. 734-739 (1995).

Naing, et al., "Safety, Antitumor Activity, and Immune Activation of Pegylated Recombinant Human Interleukin-10 (AM0010) in Patients with Advanced Solid Tumors," *Journal of Clinical Oncology*, vol. 34, No. 29, pp. 3562-3569 (2016).

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Dec. 11, 2013, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 31, 2014, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jul. 17, 2014, 6 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.

NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine Containing Regimen", ClinicalTrials.gov, Oct. 4, 2016, 3 pages.

Cindric, et al., (2007) "Structural 1-16 characterization of PEGylated rHuG-CSF and location of PEG attachment sites". Journal of Pharmaceutical and Biomedical Analysis. New York. NY. US, 44(2):388-395.

Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.

* cited by examiner

METHODS OF USING INTERLEUKIN-10 FOR TREATING DISEASES AND DISORDERS

CROSS-REFERENCE TO RELATED APPLICATION

This application claims priority benefit of U.S. provisional application Ser. No. 61/902,702, filed Nov. 11, 2013, which application is incorporated herein by reference in its entirety.

FIELD OF THE INVENTION

This invention relates to methods of using IL-10 in combination with other agents in the treatment or prevention of a diverse array of diseases and disorders, including cancers and immune-related disorders.

INTRODUCTION

The cytokine interleukin-10 (IL-10) is a pleiotropic cytokine that regulates multiple immune responses through actions on T cells, B cells, macrophages, and antigen presenting cells (APC). IL-10 can suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601).

As a result of its pleiotropic activity, IL-10 has been linked to a broad range of diseases, disorders and conditions, including inflammatory conditions, immune-related disorders, fibrotic disorders, metabolic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

In view of the diverse array of diseases, disorders and conditions susceptible to treatment or prevention with IL-10 and modified forms thereof (e.g., pegylated IL-10), combinations of IL-10 with other agents having efficacy in the treatment of fibrotic disorders and cancer, offer the potential for complementary, additive or even synergistic therapeutic regimens.

SUMMARY

The present disclosure contemplates methods of using IL-10, modified (e.g., pegylated) IL-10, and associated agents described herein, and compositions thereof, in combination with other agents to treat and/or prevent various diseases, disorders and conditions, and/or the symptoms thereof. Such combinations provide the opportunity for additive or synergistic effects in the treatment and/or prevention of the diseases, disorders and conditions described herein. Moreover, such combination therapy often allows for reductions in the amounts and/or frequencies of administration of IL-10 (e.g., PEG-IL-10) and the other agent(s) in which it is combined, which can result in any adverse effects being minimized or obviated. In particular embodiments, one or more immune checkpoint inhibitors is administered in combination with an IL-10 agent (e.g., PEG-IL-10).

Immune checkpoints refer to a large collection of inhibitory pathways integrated into the immune system that are crucial for maintaining self-tolerance and modulating the duration and amplitude of physiological immune responses in peripheral tissues in order to minimize collateral tissue damage. Tumor growth is intimately connected to regulation of immune checkpoints. Tumors assume control over certain immune-checkpoint pathways as a major mechanism of immune resistance, particularly against T cells that are specific for tumor antigens. [See, e.g., Stagg and Allard, (2013) Ther. Adv. Med. Oncol. 5(3):169-81].

Because signaling through many of the immune checkpoints is initiated by ligand-receptor interactions, it can be readily blocked by antibodies or modulated by recombinant forms of ligands or receptors. Small molecule antagonists can also find use as immune checkpoint inhibitors.

In particular embodiments, the present disclosure contemplates the administration of an IL-10 agent (e.g., PEG-IL-10) in combination with one or more immune checkpoint inhibitors for the treatment or prevention of cancer (i.e., cancerous diseases, disorders and conditions, as discussed hereafter). Such combinations can be advantageous in that the IL-10 agent and the immune checkpoint inhibitor(s) have distinct mechanisms of action, which provides the opportunity to attack the underlying disease, disorder or conditions from multiple distinct therapeutic angles. Additional advantages of such combination therapy are described elsewhere herein.

As discussed in detail hereafter, a number of immune checkpoints have been identified. Examples include, but are not limited to, PD1 (programmed cell death protein 1; also known as CD279); PDLL (PD1 ligand; also known as B7-H1); BTLA (B and T lymphocyte attenuator; also known as CD272); CTLA4 (cytotoxic T-lymphocyte associated antigen 4; also known as CD152); TIM3 (T-cell membrane protein 3; also known as HAVcr2); and LAG3 (lymphocyte activation gene 3; also known as CD233) Inhibitors of one or more of these immune checkpoints (e.g., an anti-CTLA4 antibody) are contemplated for use in the combinations and methods described herein. Multiple additional immune checkpoint receptors and ligands, some of which are selectively upregulated in various types of tumor cells, are candidates for blockade and thus are particularly suitable for combination therapy with agents like IL-10 (e.g., PEG-IL-10) that enhance the activation of antitumor responses (Pardoll, (April 2012) Nature Rev. Cancer 12:252-64).

The present disclosure also contemplates methods of identifying immune checkpoint inhibitors that are particularly suitable for use in combination with IL-10 (e.g., PEG-IL-10) for the treatment and/or prevention of the diseases, disorders and conditions described herein (e.g., cancer). Methods and models for optimizing dosing regimens for the IL-10 agents and immune checkpoint inhibitors described herein are also contemplated by embodiments of the present disclosure. In other embodiments, the present disclosure contemplates methods for the identification of specific patient populations that can optimally be suited for the combination therapies described herein. In some embodiments, the existence and/or extent of certain biomarkers can find utility in such methods.

As discussed further hereafter, human IL-10 is a homodimer, and each monomer comprises 178 amino acids, the first 18 of which comprise a signal peptide. Particular embodiments of the present disclosure comprise mature human IL-10 polypeptides lacking the signal peptide (see, e.g., U.S. Pat. No. 6,217,857), or mature human PEG-IL-10. In further particular embodiments, the IL-10 agent is a variant of mature human IL-10. The variant can exhibit activity less than, comparable to, or greater than the activity of mature human IL-10; in certain embodiments the activity is comparable to or greater than the activity of mature human IL-10.

Certain embodiments of the present disclosure contemplate modification of IL-10 in order to enhance one or more properties (e.g., pharmacokinetic parameters, efficacy, etc.). Such IL-10 modifications include pegylation, glycosylation, albumin (e.g., human serum albumin (HSA)) conjugation and fusion, and hesylation. In particular embodiments, IL-10 is pegylated. In further embodiments, modification of IL-10 does not result in a therapeutically relevant, detrimental effect on immunogenicity, and in still further embodiments modified IL-10 is less immunogenic than unmodified IL-10. The terms "IL-10", "IL-10 polypeptide(s)," "agent(s)" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, the terms "IL-10", "IL-10 polypeptide(s), "agent(s)" are agonists. Particular embodiments relate to pegylated IL-10, which is also referred to herein as "PEG-IL-10". The present disclosure also contemplates nucleic acid molecules encoding the foregoing.

Particular embodiments of the present disclosure relate to methods of treating or preventing a disease, disorder or condition (e.g., a cancer) in a subject (e.g., a human), comprising administering to the subject a therapeutically effective amount of an IL-10 agent (e.g., PEG-IL-10) and an immune checkpoint inhibitor, wherein the therapeutically effective amount of the IL-10 agent is sufficient to achieve a mean IL-10 serum trough concentration from 1 pg/mL to 10.0 ng/mL. In some embodiments, the mean IL-10 serum trough concentration of from 1.0 pg/mL to 10.0 ng/mL is maintained for at least 95% of the period of time.

In some embodiments of the present disclosure, the mean IL-10 serum trough concentration is in the range of from 1.0 pg/mL to 100 pg/mL; from 0.1 ng/mL to 1.0 ng/mL; from 1.0 ng/mL to 10 ng/mL; from 0.5 ng/mL to 5.0 ng/mL; from 0.75 ng/mL to 1.25 ng/mL or from 0.9 ng/mL to 1.1 ng/mL. In particular embodiments of the present disclosure, the mean IL-10 serum trough concentration is at least 1.25 ng/mL, at least 1.5 ng/mL, at least 1.6 ng/mL, at least 1.7 ng/mL, at least 1.8 ng/mL, at least 1.85 ng/mL, at least 1.9 ng/mL, at least 1.95 ng/mL, at least 1.97 ng/mL, and least 1.98 ng/mL, at least 1.99 ng/mL, at least 2.0 ng/mL or greater than 2 ng/mL.

In further embodiments, the aforementioned period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, at least 6 months, at least 9 months, or greater than 12 months.

In particular embodiments of the present disclosure, the mean IL-10 serum trough concentration is maintained for at least 85% of the period of time, at least 90%, at least 96%, at least 98%, at least 99% or 100% of the period of time.

It is envisaged that a dosing regimen sufficient to maintain a desired steady state serum trough concentration (e.g., 1 ng/mL) can result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (amount and frequency) are kept constant. After that period to time, the gradual but continual decrease ends and a steady state serum trough concentration is maintained.

By way of example, parenteral administration (e.g., SC and IV) of ~0.1 mg/kg/day of an IL-10 agent (e.g., mIL-10) to a mouse (e.g., a C57BL/6 mouse) is required to maintain a steady state serum trough concentration of 2.0 ng/mL. However, that steady state serum trough concentration cannot be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of, for example, the approximately 30-day period, after which time the desired steady state serum trough concentration (2.0 ng/mL) is maintained. One of skill in the art will be able to determine the dose needed to maintain the desired steady state trough concentration using, for example, ADME and patient-specific parameters.

Certain embodiments of the present disclosure are directed to dosing parameters, regimens and the like for the immune checkpoint inhibitors when they are administered in combination with IL-10 (e.g., PEG-IL-10). In general, the dosing parameters and treatment regimens associated with immune checkpoint inhibitor monotherapy are applicable when such agents are used in conjunction with an IL-10 agent described herein.

The present disclosure contemplates methods wherein the IL-10 agent comprises at least one modification to form a modified IL-10 agent, wherein the modification does not alter the amino acid sequence of the IL-10 agent. In some embodiments, the modified IL-10 agent is a PEG-IL-10 agent. The PEG-IL-10 agent can comprise at least one PEG molecule covalently attached to at least one amino acid residue of at least one subunit of IL-10 or comprise a mixture of mono-pegylated and di-pegylated IL-10 in other embodiments. The PEG component of the PEG-IL-10 agent can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

In some embodiments, the modified IL-10 agent comprises at least one Fc fusion molecule, at least one serum albumin (e.g., HSA or BSA), an HSA fusion molecule or an albumin conjugate. In additional embodiments, the modified IL-10 agent is glycosylated, is hesylated, or comprises at least one albumin binding domain. Some modified IL-10 agents can comprise more than one type of modification. In particular embodiments, the modification is site-specific.

Some embodiments comprise a linker. Modified IL-10 agents are discussed in detail hereafter.

Certain embodiments of the present disclosure contemplate the administration of an IL-10 agent (e.g., PEG-IL-10) in combination with one immune checkpoint inhibitor, other embodiments contemplate the administration of an IL-10 agent in combination with two immune checkpoint inhibitors, and still further embodiments contemplate the administration of an IL-10 agent in combination with three or more immune checkpoint inhibitors. Such combinations can be advantageous in that the IL-10 agent and the immune checkpoint inhibitor(s) have distinct mechanisms of action, which provides the opportunity to attack the underlying disease, disorder or conditions from multiple distinct therapeutic angles. Additional advantages of such combination therapy are described elsewhere herein.

The specific IL-10 and immune checkpoint inhibitor(s) (along with, e.g., the therapeutic goal) influence the dosing regimens, parameters, etc. when they are used in combination. In some embodiments, the present disclosure contemplates methods wherein PEG-IL-10 can be administered to a subject at least twice daily, at least once daily, at least once every 48 hours, at least once every 72 hours, at least once weekly, at least once every 2 weeks, at least once monthly, at least once every 2 months, or at least once every 3 months or longer. In certain embodiments, the PEG-IL-10 can be administered in combination with the immune checkpoint inhibitor ipilimumab (YERVOY, Bristol-Myers Squibb), a recombinant, human monoclonal antibody that binds to the cytotoxic T-lymphocyte-associated antigen 4 (CTLA4). The recommended dose of ipilimumab is 3 mg/kg administered intravenously every 3 weeks for a total of 4 doses. In an exemplary embodiment, combination therapy comprising PEG-IL-10 and ipilimumab can be initiated at or about the same time. In another exemplary embodiment comprising combination therapy with PEG-IL-10 and ipilmumab, ipilimumab therapy (administration every 3 weeks) can be initiated first, and weekly PEG-IL-10 therapy can be initiated one week thereafter, two weeks after which the second dose of ipilimumab is administered. In some embodiments, the therapeutic regimen comprises a wash-out period ("drug holiday") wherein the serum level of PEG-IL-10, ipilimumab, or both decreases to a desired level to allow the subject to recover from any adverse effects associated with the ipilimumab (e.g., immune-related adverse reactions). The skilled artisan (e.g., an oncologist) will be able to tailor a treatment regimen that takes into consideration the characteristics of the IL-10 and immune checkpoint inhibitor agents (e.g., their pharmacokinetic parameters), patient-specific characteristics (e.g., renal function), and goals of therapy.

Particular embodiments of the present disclosure contemplate the administration of one or more additional agents (e.g., chemotherapeutic agents) with the combinations of an IL-10 agent and one or more immune checkpoint inhibitors described herein. The identity of the additional agent(s) will be largely dependent on the nature of the underlying condition being treated (e.g., the addition of an alkylating agent such as cisplatin may be appropriate in the treatment of bladder cancer). Embodiments wherein one or more additional therapeutic or prophylactic agents (e.g., chemotherapeutic agents) are administered in conjunction with the combinations of an IL-10 agent and one or more immune checkpoint inhibitors are described further hereafter.

The IL-10 agent can be administered by any effective route. In some embodiments, it is administered by parenteral injection, including subcutaneous injection in certain embodiments. The one or more immune checkpoint inhibitors may also be administered by any route effective in view of the nature of the inhibitor. In some embodiments, the IL-10 agent and the immune checkpoint inhibitor(s) can be administered by the same route (e.g., SC), while in other embodiments they can be administered by different routes (e.g., the IL-10 agent can be administered subcutaneously and the immune checkpoint inhibitor(s) can be administered intravenously.

Particular embodiments of the present disclosure are directed to pharmaceutical compositions comprising a therapeutically acceptable amount of an IL-10 agent in combination with a therapeutically acceptable amount of an immune checkpoint inhibitor(s), along with one or more pharmaceutically acceptable diluents, carriers and/or excipients (e.g., an isotonic injection solution). The pharmaceutical composition is generally one that is suitable for human administration. Furthermore, in some embodiments the pharmaceutical composition comprises at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container can be a syringe. In still further embodiments, the sterile container is one component of a kit; the kit can also contain, for example, a second sterile container that comprises at least one prophylactic or therapeutic agent, examples of which are set forth herein.

DETAILED DESCRIPTION

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The vast majority of cancer cells have a large number of inherent genetic and epigenetic changes which provide numerous tumor-associated antigens that the host immune system can recognize, thereby requiring tumors to develop specific immune resistance mechanisms in order to proliferate. Immune checkpoints, also referred to as immune-inhibitory pathways, are an important immune resistance mechanism that normally mediates immune tolerance and mitigates collateral tissue damage.

In humans suffering from cancer, antitumor immunity is often ineffective due to the tight regulation associated with the maintenance of immune homeostasis. One of the major limitations is the process of "T-cell exhaustion", which results from chronic exposure to antigens and is characterized by the upregulation of inhibitory receptors. These inhibitory receptors serve as immune checkpoints to prevent uncontrolled immune reactions. Blocking one or more of these immune checkpoints with monoclonal antibodies (mAbs) has been shown to rescue otherwise exhausted anti-tumor T cells and has been associated with objective clinical responses in cancer patients (Stagg and Allard, (2013) Ther. Adv. Med. Oncol. 5(3):169-81). Thus, inhibition of immune checkpoints offers a promising new avenue for the treatment of certain cancers.

The present disclosure contemplates the use of the IL-10 agents described herein (e.g., PEG-IL-10), and compositions thereof, in combination with one or more immune checkpoint inhibitors to treat and/or prevent various diseases, disorders and conditions (e.g., cancers), and/or the symptoms thereof. In certain aspects of the present disclosure, such treatment or prevention is effected by utilizing particular dosing parameters that serve to minimize any adverse effects associated with administration of the individual therapies by themselves. By way of example, the addition of a PEG-IL-10 regimen to a regimen comprising ipilimumab (an anti-CTLA4 mAb) might allow a reduction of the amount of ipilimumab needed to achieve the therapeutic goal, thus reducing (or even eliminating) ipilimumab's severe and fatal immune-mediated adverse reactions that prompted the FDA to require a "black box warning".

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it can correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule can be more permeable to cells, less susceptible to degradation, and less likely to elicit an immune response than large molecules.

The term "ligand" refers to, for example, peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor can be entirely intracellular, that is, it can reside in the cytosol, nucleus, or some other intracellular compartment. The complex of a ligand and receptor is termed a "ligand-receptor complex."

The terms "inhibitors" and "antagonists", or "activators" and "agonists", refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor can also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-10 agent (or the nucleic acid molecules encoding them), either directly or indirectly; or to enhance the ability of a molecule to produce an effect comparable to that of an IL-10 agent. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator can act alone, or it can use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule can describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term can also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect can refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
|---|---|---|---|---|---|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 dimer becomes biologically inactive upon disruption of the non-covalent interactions between the two monomer subunits.

The present disclosure contemplates human IL-10 (NP_000563) and murine IL-10 (NP_034678), which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

As alluded to above, the terms "IL-10", "IL-10 polypeptide(s), "IL-10 molecule(s)", "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which can be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity.

As used herein, the terms "pegylated IL-10" and "PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. As used herein, the terms "dipegylated IL-10" and "di-PEG-IL-10" indicate that at least one polyethylene glycol molecule is attached to a single residue on each subunit of the IL-10 dimer, generally via a linker.

In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein.

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some can be post-translational variants, e.g., glycosylated variants. Any variant of IL-10 can be used provided it retains a suitable level of IL-10 activity.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides can be isolated from a natural source (e.g., an environment other than its naturally-occurring environment) and can also be recombinantly made (e.g., in a genetically modified host cell such as bacteria, yeast, *Pichia*, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

Immune Checkpoint Inhibitors

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor-ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

IL-10 has been shown to directly activate the cytotoxicity of human and murine CD8+ T cells through the direct upregulation of the cytotoxic enzymes granzyme A, granzyme B, and perforin. In addition, under appropriate conditions, exposure of these cells to IL-10 enhances the intracellular accumulation of IFNγ, which can be secreted upon T-cell receptor ligation with soluble anti-CD3 or cognate MHC I loaded with peptide antigen. Whereas IL-10 (e.g., PEG-IL-10) directly enhances CD8+ T cell function, as indicated above, immune checkpoint inhibitors generally do so in an indirect manner. The divergent mechanisms by which IL-10 and immune checkpoint inhibitors exert there effects on CD8+ T cell function offer an untapped opportunity for combination therapy having potentially powerful therapeutic results.

Examples of immune checkpoints (ligands and receptors), some of which are selectively upregulated in various types of tumor cells, that are candidates for blockade include PD1, PDL1, BTLA, CTLA4, TIM3, LAG3; A2aR; and Killer Inhibitory Receptors. Each of these is discussed below. The present disclosure contemplates the use of IL-10 agents (e.g., PEG-IL-10) in combination with inhibitors of these and other immune-checkpoint receptors and ligands. In the tumor setting, a primary therapeutic goal of these IL-10-immune checkpoint inhibitor combinations is to direct the CD8+ compartment to destroy the tumor.

CTLA4 (cytotoxic T-lymphocyte associated antigen 4; also known as CD152). The immune checkpoint receptor CTLA4 belongs to the immunoglobulin superfamily of receptors, which also includes PD1; BTLA; lymphocyte attenuator; TIM3, and V-domain immunoglobulin suppressor of T cell activation. CD80 (also known as B7.1) and CD86 (also known as B7.2) have been identified as the CTLA4 receptor ligands. CTLA4, the first immune checkpoint receptor to be clinically targeted, is expressed exclusively on T cells, where it primarily regulates the amplitude of the early stages of T cell activation. It has been shown to counteract the activity of the T cell co-stimulatory receptor CD28. Upon antigen recognition, CD28 signaling strongly amplifies T-cell receptor signaling to activate T cells. [See, e.g., Riley et al., (2002) Proc. Natl Acad. Sci. USA 99:11790-95].

CTLA4 is transcriptionally induced following T cell activation. Although CTLA4 is expressed by activated CD8+ effector T cells, its primary physiological role is believed to be manifested through distinct effects on the two major subsets of CD4+ T cells: i) down-modulation of helper T cell activity, and ii) enhancement of regulatory T cell immunosuppressive activity. Specifically, CTLA4 blockade results in immune response enhancement dependent on helper T cells, while CTLA4 engagement of regulatory T cells increases their suppressive function. [See, e.g., Fontenot et al., (2003) Nat. Immunol. Proc. 4:330-36].

Various experimental approaches have been described targeting the CTLA4 signaling pathway using anti-CTLA4 antagonistic antibodies. These approaches have been evaluated to discern the potential utility of such antibodies in cancer (e.g., tumor) and infectious conditions. For example, IL-10 has previously been implicated in CTLA4-mediated suppression of anti-tumor immune responses (Jovasevic et al., (2004) J. Immunol. 172:1449-54). When it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Another agent, tremelimumab (formerly ticilimumab; MedImmune) is currently in clinical trials for, for example, hepatocellular carcinoma, melanoma and mesothelioma.

The CD28 signaling pathway has also been targeted using antagonistic CTLA4-Ig for potential utility in autoimmune and transplantation conditions (Wu et al., (2012) Int. J. Biol. Sci. 8:1420-30). Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus.

Though promising, CTLA4-related treatment approaches are not without shortcomings. By way of example, treatment of metastatic melanomas with a humanized anti-CTLA4 antagonistic Ab has been reported to cause certain autoimmune toxicities (e.g., bowel inflammation and dermatitis), prompting the determination of a tolerated therapeutic window (Wu et al., (2012) Int. J. Biol. Sci. 8:1420-30). Combination of an anti-CTLA4 agent (e.g., an antibody such as ipilimumab) with IL-10 (e.g., PEG-IL-10) offers the potential for a unique means of maximizing therapeutic efficacy in responsive conditions without inducing intolerable adverse effects. Accordingly, particular embodiments of the present disclosure comprise such combinations.

PD1 (programmed cell death protein 1; also known as CD279), and PDL1 (PD1 ligand; also known as B7-H1) and PDL2. PD1 is a negative regulator of T cell activation that shares structural properties with members of the CD28 family. PD1 limits T cell effector functions within tissues. By up-regulating ligands for PD1, tumor cells block antitumor immune responses in the tumor microenvironment. As with many other immune checkpoint inhibitors, PD1 blockade reverses T cell exhaustion, restores cytokine production, and augments the expansion of antigen-dependent T cells. PDL1 and PDL2 are the two ligands known to activate the PD1 pathway.

Blockade of the PD1-PDL1/PDL2 pathway has been shown to delay tumor growth and prolong the survival of tumor-bearing mice. In addition, the results of early-stage clinical trials suggested that blockade of the PD1 pathway induced sustained tumor regression in a variety of tumor types. For PD1 and PDL1/PDL2, the most important interaction is believed to be at the tumor site, rather than more broadly across the immune system as it is with CTLA-4.

Various immunotherapeutic approaches that modulate the PD1-PDL1/PDL2 pathway using gene transfer and/or antagonistic antibodies have been evaluated. Such approaches have shown promise in a number of diseases, disorders and conditions, including transplantation, infection, tumor, and autoimmune disease (Wu et al., (2012) Int. J. Biol. Sci. 8:1420-30). The extracellular immunoglobulin (Ig) V domain of PD1 has been shown to be important for the interaction between PD1 and PDL1/PDL2, suggesting that hPD1-IgV can be a promising strategy for specific tumor immunotherapy (Zhang et al., (2008) Cytotherapy 10(7):711-10). PD1 antibodies are under development (e.g., nivolumab (Bristol-Myers Squibb), pidilizumab (CT-011; CureTech) and lambrolizumab (Merck)). Nivolumab has shown promise in patients with melanoma, lung and kidney cancer. Combination therapy comprising nivolumab and the CTLA-4 modulator ipilimumab is also being evaluated in lung cancer. Anti-PDL1 antibodies are also being evaluated (e.g., BMS-936559 (Bristol-Myers Squibb), MPDL3280A (Genentech/Roche) and MEDI4736 (MedImmune)), as are anti-PDL2 antibodies (e.g, AMP-224 (Amplimmune/GlaxoSmithKline)).

IL-10 has been implicated in the inhibitory effects of PD1/PDL1 ligation (see Said et al., (2010) Nat. Med. 16:452-59; Wolfle et al., (2011) Eur. J. Immunol. 41:413-24; Rodriguez-Garcia et al., (April 2011) J. Leukoc. Biol. 89(4): 507-15; and Getts et al., (2011) J. Immunol. 187:2405-17). In contrast to the suggestions in the literature, the present disclosure contemplates a promising therapeutic approach comprising the combination of an IL-10 agent (e.g. PEG-IL-10) with an inhibitor of PD1, PD1L or the direct interaction between PD1/PDL1.

BTLA (B and T lymphocyte attenuator; also known as CD272). BTLA is a co-inhibitory molecule structurally and functionally related to CTLA-4 and PD-1. Although BTLA is expressed on virus-specific human CD8+ T cells, it is progressively downregulated after their differentiation from a naive to effector phenotype (Paulos et al., (January 2010) J. Clin. Invest. 120(1):76-80). The herpes virus entry mediator (HVEM; also known as TNFRSF14), which is expressed on certain tumor cell types (e.g., melanoma) and tumor-associated endothelial cells, has been identified as the BTLA ligand. Because the interactions between BTLA and HVEM are complex, therapeutic inhibition strategies are less straightforward for BTLA than they are for other immune checkpoint inhibitory receptors and ligands. [Pardoll, (April 2012) Nature Rev. Cancer 12:252-64].

A number of experimental approaches targeting the BTLA/HVEM pathway using anti-BTLA antibodies and antagonistic HVEM-Ig have been evaluated, and such approaches have suggested promising utility in a number of diseases, disorders and conditions, including transplantation, infection, tumor, and autoimmune disease (Wu et al., (2012) Int. J. Biol. Sci. 8:1420-30).

The cross-linking of BTLA with an agonist antibody has been shown to limit T cell proliferation, IFNγ and IL-10 secretion (Otsuki et al., (2006) BBRC 344:1121-27). In addition, IL-10 exposure was shown to consistently downregulate message expression of BTLA in CD8+ T cells. Taken together, these data suggest a possible converse regulation of IL-10 and BTLA, and particular embodiments of the present disclosure contemplate administering a combination of IL-10 (e.g., PEG-IL-10) and an anti-BTLA agent to a subject having a disease, disorder or condition response to such combination therapy.

TIM3 (T-cell membrane protein 3; also known as HAVcr2). TIM3 inhibits T helper 1 (TH1) cell responses, and TIM3 antibodies have been shown to enhance antitumor immunity. The ligand for TIM3, galectin 9, is upregulated in various types of cancer, including breast cancer.

TIM3 has been reported to be co-expressed with PD1 on tumor-specific CD8+ T cells. When stimulated by the cancer-testes antigen NY-ESO-1, dual blockade of both molecules significantly enhances the in vitro proliferation and cytokine production of human T cells. Moreover, in animal models, coordinate blockade of PD1 and TIM3 was reported to enhance antitumor immune responses in circumstances in which only modest effects from blockade of each individual molecule were observed. [See, e.g., Pardoll, (April 2012) Nature Rev. Cancer 12:252-64; Zhu et al., (2005) Nature Immunol. 6:1245-52; Ngiow et al., (2011) Cancer Res. 71:3540-51)].

TIM-3 blockade has been shown to upregulate IL-10 (see Zhang, (2012) J. Leukoc. Biol. 91(2):189-96; Anderson, (2010) Eur. J. Immunol. 40:859-66). Though neither described nor suggested in the literature, this finding supports the possibility that there can exist a potent synergy when an anti-TIM3 agent (e.g., a neutralizing Ab) is administered as part of a therapeutic regimen comprising IL-10.

LAG3 (lymphocyte activation gene 3; also known as CD233). LAG3 has been shown to play a role in enhancing the function of Regulatory T ($T_{Reg}$) cells, and independently in inhibiting CD8+ effector T cell functions. MHC class II molecules, the ligand for LAG3, are upregulated on some epithelial cancers (often in response to IFNγ), and are also expressed on tumor-infiltrating macrophages and dendritic cells. Though the role of the LAG3-MHC class II interaction has not been definitively elucidated, the interaction can be a key component in the role of LAG3 in enhancing $T_{Reg}$ cell function.

LAG3 is one of several immune checkpoint receptors that are coordinately upregulated on both $T_{Reg}$ cells and anergic T cells. Simultaneous blockade of LAG3 and PD1 can cause enhanced reversal of the anergic state when compared to blockade of one receptor alone. Indeed, blockade of LAG3 and PD1 has been shown to synergistically reverse anergy among tumor-specific CD8+ T cells and virus-specific CD8+ T cells in the setting of chronic infection. IMP321 (ImmuFact) is being evaluated in melanoma, breast cancer, and renal cell carcinoma. [See generally Woo et al., (2012) Cancer Res 72:917-27; Goldberg et al., (2011) Curr. Top. Microbiol. Immunol. 344:269-78; Pardoll, (April 2012) Nature Rev. Cancer 12:252-64; Grosso et al., (2007) J. Clin. Invest. 117:3383-392].

LAG3 has also been shown to be a marker for IL-10 expressing $T_{Reg}$ cells (Camisaschi et. al., (2010) J. Immunol. 184). These LAG3-positive cells have been shown to be increased in cancer patients, and there is the belief that IL-10 is involved in promoting immune suppression. A particular embodiment of the present disclosure contemplates combination therapy comprising LAG3 and IL-10.

A2aR (adenosine A2a receptor A2aR; also known as Adora2a). A2aR inhibits T cell responses by stimulating CD4+ T cells towards developing into $T_{Reg}$ cells. A2aR is particularly important in tumor immunity because the rate of cell death in tumors from cell turnover is high, and dying cells release adenosine, which is the ligand for A2aR. In addition, deletion of A2aR has been associated with enhanced and sometimes pathological inflammatory responses to infection.

Inhibition of A2aR can be effected by antibodies that block adenosine binding or by adenosine analogs. Such agents can be useful in disorders such as cancer and Parkinson's disease. [See generally, Zarek et al., (2008) Blood 111:251-59; Waickman et al., (25 Nov. 2011) Cancer Immunol. Immunother. (doi: 10. 1007/s00262-011-1155-7)]. Combination therapy with such agents and IL-10 are specifically contemplated by the present disclosure.

Killer Inhibitory Receptors. Killer inhibitory receptors can be divided into two classes based on their structural features: i) killer cell immunoglobulin-like receptors (KIRs), and ii) C-type lectin receptors (members of the type II transmembrane receptor family). Although the roles of these receptors are still being investigated, they are known to be important regulators of the killing activity of NK cells, and activation of NK cells can provide potent antitumor activity. They are also believed to play an inhibitory role on T cells and APCs (e.g., dendritic cells). KIR IgG4 (lirilumab; Bristol-Myers Squibb) is being investigated in lung cancer.

Although the majority of killer inhibitory receptors are specific for subsets of human leukocyte antigens (e.g., HLA) and possess allele-specificity, others recognize broadly-expressed molecules Inhibition of members of the family of NK cells can present a unique approach to modulating anti-tumor immune responses, and combination therapy comprising an IL-10 agent (e.g., PEG-IL-10) is an embodiment of the present disclosure. [See Raulet, (2006) Semm. Immunol. 18:145-50; Plougastel et al., (2006) Curr. Top. Microbiol. Immunol. 298:77-89].

Additional Immune Checkpoints. Other less-defined immune checkpoints have been described in the literature. They include both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64]. B7-H3 and B7-H4 are members of the B7 superfamily that includes CTLA4 and PD1. B7-H3, a ligand that inhibits T-cell activation, is being evaluated in several refractory cancers (MGA271; MacroGenics).

IDO (Indoleamine 2,3-dioxygenase) is an immune regulatory enzyme that is normally expressed in tumor cells and in activated immune cells. IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Indoximod (NewLink Genetics) is an IDO inhibitor being evaluated in metastatic breast cancer.

The present disclosure contemplates the use of inhibitors of these and other immune checkpoints, known and yet-to-be fully elucidated and/or identified, in combination with the IL-10 agents (e.g., PEG-IL-10) described herein.

Therapeutic Considerations. Many tumor cells express multiple inhibitory ligands, and tumor-infiltrating lymphocytes (TILs) express multiple inhibitory receptors. When considering the mechanisms of action of inhibitors of various immune checkpoints, the diversity of immune functions that they regulate comes into play. For example, CTLA4 and PD1 regulate immune responses at different levels and by different mechanisms. Thus, antitumor immunity can be enhanced at multiple levels, and combinatorial strategies can be generated in view of various mechanistic considerations.

In view of the above, in many instances antitumor immunity can be enhanced through dual or triple (or possibly more) blockade of immune checkpoints. Multi-specific antibodies have been disclosed in the art. For example, US Patent Publn. 2013/0156774 describes bispecific and multispecific agents (e.g., antibodies), and methods of their use, for targeting cells that co-express PD1 and TIM3. Moreover, dual blockade of BTLA and PD1 has been shown to enhance antitumor immunity (Pardoll, (April 2012) Nature Rev. Cancer 12:252-64).

The present disclosure contemplates the use of IL-10 (e.g., PEG-IL-10) in combination with the strategies outlined above for targeting multiple immune checkpoint inhibitors.

Therapeutic responses to immune checkpoint inhibitors generally manifest themselves much later than responses to traditional chemotherapies and tyrosine kinase inhibitors. Indeed, it can take six months or more after treatment initiation with immune checkpoint inhibitors before objective indicia of a therapeutic response are observed. In addition, in some cases involving anti-CTLA4 antibody therapy, metastatic lesions actually increase in size on computed tomography (CT) or magnetic resonance imaging (MRI) scans before subsequently regressing; this appears to be due to increased immune cell infiltration. [See, e.g., Pardoll, (April 2012) Nature Rev. Cancer 12:252-64]. Therefore, a determination as to whether treatment with an immune checkpoint inhibitor(s) in combination with an IL-10 agent of the present disclosure (e.g., PEG-IL-10) must be made over a time-to-progression that is frequently longer than with convention therapies.

Methods and Models Associated with Immune Checkpoint Inhibitors. The present disclosure contemplates various methods and models for identifying candidate subject populations (or individual subjects) having a disease(s), disorder(s) or condition(s) that can be responsive to the combination therapies described herein (i.e., IL-10 (e.g., PEG-IL-10) in combination with an immune checkpoint inhibitor(s)). In some embodiments, the methods and models allow a determination of whether administration of the combination results in an additive or synergistic effect. In other embodiments, the methods and models allow a determination of whether administration of the combination results in fewer adverse effects. Certain embodiments of the present disclosure comprise the use of in vitro, ex vivo and in vivo methods and/or models. The subject population (or individual subject) is a non-human animal (e.g., rodent) or human in certain embodiments of the present disclosure.

By way of example, but not limitation, one aspect of the present disclosure contemplates a method for determining whether a test subject having a disease, disorder or condition described herein (e.g., a cancerous condition) is a candidate for treatment with a combination of IL-10 (e.g., PEG-IL-10) and an immune checkpoint inhibitor(s), the method comprising a) providing a test subject having an indicia of such a disease, disorder or condition, b) co-administering the combination to the test subject, wherein the combination is sufficient to achieve a desired response in a reference population, and c) determining whether the test subject exhibits the desired response; wherein the determination of the desired response indicates that the test subject is a candidate for treatment with the combination.

The desired response can be any result deemed favorable under the circumstances. In some embodiments, the desired response is prevention of the progression of the disease, disorder or condition, while in other embodiments the desired response is a regression or stabilization of one or more characteristics of the disease, disorder or conditions (e.g., reduction in tumor size). In still other embodiments, the desired response is reduction or elimination of one or more adverse effects associated with one or more agents of the combination.

As indicated above, the present disclosure also contemplates various models. Any model can be used that provides reliable, reproducible results. The skilled artisan is familiar with models that can be used in conjunction with the subject matter of the present disclosure; in one embodiment, the combination is evaluated in a model comprising a non-human subject (e.g., a mouse). Particular embodiments of the present disclosure contemplate a model for determining whether a combination of IL-10 and one or more immune checkpoint inhibitors is a candidate for treating a disease, disorder or condition described herein (e.g., a cancerous condition).

Further embodiments comprise a method or model for determining the optimum amount of an agent(s) in a combination. An optimum amount can be, for example, an amount that achieves an optimal effect in a subject or subject population, or an amount that achieves a therapeutic effect while minimizing or eliminating the adverse effects associated with one or more of the agents. In some embodiments, the combination of IL-10 and immune checkpoint inhibitor(s) itself is known to be, or has been determined to be, effective in treating or preventing a disease, disorder or condition described herein (e.g., a cancerous condition) in a subject (e.g., a human) or a subject population, and an amount of one agent is titrated while the amount of the other agent(s) is held constant. By manipulating the amounts of the agent(s) in this manner, a clinician is able to determine the ratio of agents most effective for, for example, treating a particular disease, disorder or condition, or eliminating the adverse effects or reducing the adverse effects such that are acceptable under the circumstances.

Biomarkers Associated with Immune Checkpoint Inhibitors. The present disclosure also contemplates the use of biomarkers in conjunction with the methods and models described herein. The term "biomarker(s)" refers to a characteristic that is objectively measured and evaluated as an indicator of normal biological processes, pathogenic processes, or pharmacologic responses to a therapeutic intervention. The indicator may be any substance, structure, or process that can be measured in the body or its products and influences or predicts the incidence of outcome or disease.

In some embodiments of the present disclosure contemplate, a biomarker(s) is used to predict a clinical response(s) to IL-10-immune checkpoint inhibitor combination therapy. In some instances, a pre-treatment biomarker can be used in such therapy wherein the biomarker has been validated to the point at which it could be applied as part of standard-of-care therapeutic decision-making.

The present disclosure contemplates the use of any biomarker that can provide reproducible information useful in any aspect of IL-10-immune checkpoint inhibitor therapy, including the existence and extent of a subject's response to such therapy and the existence and extent of untoward effects caused by such therapy. By way of example, but not limitation, biomarkers associated with PD1/PDL1 include enhancement of IFNγ, and upregulation of granzyme A, granzyme B, and perforin; biomarkers associated with BTLA include an increase in CD8+ T cell number and function; biomarkers associated with CTLA4 include enhancement of IFNγ, upregulation of granzyme A, granzyme B, and perforin, and an increase in ICOS expression on CD8+ T cells; biomarkers associated with TIM3 include upregulation of granzyme A, granzyme B, and perforin; and biomarkers associated with LAG3 include enhancement of IL-10 expressing $T_{Reg}$ cells. Expression of the effector molecules IP-10 (Inducible Protein 10) and MIG (Monokine Induced by IFNγ) are known to be increased in certain IL-10-expressing tumors by either LPS or IFNγ; these effector molecules can also be leveraged as potential serum biomarkers that may be enhanced by the combinatorial therapies described herein.

Serum Concentrations

The blood plasma levels of IL-10 in the methods described herein can be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, mean serum trough IL-10 concentrations have been found to be of particular import for efficacy in certain indications.

In some embodiments of the present disclosure, blood plasma and/or serum level concentration profiles that can be produced include: a mean IL-10 plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL.

In particular embodiments of the present disclosure, a mean IL-10 serum trough concentration is in the range of from 1.0 pg/mL to 10 ng/mL. In some embodiments, the mean IL-10 serum trough concentration is in the range of from 1.0 pg/mL to 100 pg/mL. In other embodiments, the mean IL-10 serum trough concentration is in the range of from 0.1 ng/mL to 1.0 ng/mL. In still other embodiments, the mean IL-10 serum trough concentration is in the range of from 1.0 ng/mL to 10 ng/mL. It is to be understood that the present disclosure contemplates ranges incorporating any concentrations encompassed by those set forth herein even if such ranges are not explicitly recited. By way of example, the mean serum IL-10 concentration in an embodiment can be in the range of from 0.5 ng/mL to 5 ng/mL. By way of further examples, particular embodiments of the present disclosure comprise a mean IL-10 serum trough concentration in a range of from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL.

In particular embodiments, a mean IL-10 serum trough concentration of 1-2 ng/mL is maintained over the duration of treatment. The present disclosure also contemplates embodiments wherein the mean IL-10 serum peak concentration is less than or equal to about 10.0 ng/mL over the duration of treatment. Further embodiments contemplate a mean IL-10 serum trough concentration greater than or equal to about 1.0 pg/mL. The optimal mean serum concentration is generally that at which the desired therapeutic effect is achieved without introducing undesired adverse effects.

Certain embodiments of the present disclosure provide a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. In particular subject populations, a smaller peak-trough fluctuation indicates a lower probability that the subject will experience IL-10-related adverse effects. In addition, in some embodiments particular peak-trough fluctuations are determined for the treatment of particular diseases, disorders and conditions using particular dosing parameters, and those fluctuations are used as reference standards.

For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Thus, volume-of-distribution considerations are pertinent when assessing appropriate IL-10 dosing-related parameters. Moreover, efforts to target IL-10 agents to specific cell types have been explored (see, e.g., Rachmawati, H. (May 2007) Drug Met. Dist. 35(5):814-21), and the leveraging of IL-10 pharmacokinetic and dosing principles can prove invaluable to the success of such efforts.

The present disclosure contemplates administration of any dose and dosing regimen that results in maintenance of any of the IL-10 serum trough concentrations set forth above. By way of example, but not limitation, when the subject is a human, non-pegylated hIL-10 can be administered at a dose greater than 0.5 μg/kg/day, greater than 1.0 μg/kg/day, greater than 2.5 μg/kg/day, greater than 5 μg/kg/day, greater than 7.5 μg/kg, greater than 10.0 μg/kg, greater than 12.5 μg/kg, greater than 15 μg/kg/day, greater than 17.5 μg/kg/day, greater than 20 μg/kg/day, greater than 22.5 μg/kg/day, greater than 25 μg/kg/day, greater than 30 μg/kg/day, or greater than 35 μg/kg/day. In addition, by way of example, but not limitation, when the subject is a human, pegylated hIL-10 comprising a relatively small PEG (e.g., 5 kDa mono-di-PEG-hIL-10) can be administered at a dose greater than 0.5 µg/kg/day, greater than 0.75 µg/kg/day, greater than 1.0 µg/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 µg/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day.

Although the preceding discussion regarding IL-10 serum concentrations, doses and treatment protocols that are necessary to achieve particular IL-10 serum concentrations, etc., pertains to monotherapy with an IL-10 agent (e.g., PEG-IL-10), in certain embodiments such doses, treatment protocols, etc. are also relevant to therapeutic regimens comprising an IL-10 agent in combination with one or more immune checkpoint inhibitors. For example, a PEG-IL-10 dosing regimen may be the same when it is administered alone or when it is administered in combination with a PD1 antagonist because the PEG-IL-10 and PD1 antagonist have distinct mechanisms of action that allow the agents to be combined without modifications to their dosing parameters. However, such combinations can allow for modifications to the normal dosing regimen of the PEG-IL-10 and/or the immune checkpoint inhibitor(s). For example, the therapeutic dose of one or both of the agents can be reduced, the frequency of dosing of one or both agents can be decreased, and/or the duration of therapy of one or both of the agents can be shortened, while retaining the desired therapeutic effect.

The skilled artisan (e.g., a pharmacologist) is able to determine the optimum dosing regimen(s) when an IL-10 agent (e.g., PEG-IL-10) is administered in combination with an immune checkpoint inhibitor(s). By way of example, in some embodiments the optimum PEG-IL-10 dosing regimen may require a reduction in the amount of PEG-IL-10 administered per dose (e.g., less than 1.0 µg/kg/day, less than 0.75 µg/kg/day, less than 0.5 µg/kg/day, less than 0.25 µg/kg/day, or less than 0.125 µg/kg/day). In certain exemplary embodiments of the present disclosure, a mean IL-10 serum trough concentration may be in a range of from about 0.1 ng/mL to about 9.5 ng/mL, from about 0.25 ng/mL to about 8.0 ng/mL, from about 0.5 ng/mL to about 7.0 ng/mL, from about 0.75 ng/mL to about 6.0 ng/mL, or from about 1.0 ng/mL to about 5.0 ng/mL.

When an IL-10 agent is administered in combination with an immune checkpoint inhibitor, one or more of the dosing parameters of the IL-10 agent applicable to monotherapy can be modified while the dosing parameters of the immune checkpoint inhibitor(s) applicable to monotherapy can remain the same; one or more of the dosing parameters of the IL-10 agent applicable to monotherapy can remain the same while one or more the dosing parameters of the immune checkpoint inhibitor(s) applicable to monotherapy can be modified; one or more of the dosing parameters of the IL-10 agent and the immune checkpoint inhibitor(s) applicable to monotherapy can be modified; or the dosing parameters of each of the IL-10 agent and the immune checkpoint inhibitor(s) applicable to monotherapy can remain the same.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis can be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α, α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, 0-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide can be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH2NH—, —CH2S—, —CH2CH2-, —CH═CH-(cis and trans), —COCH2-, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine(sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$—CO— or —(CH2)$_n$—C$_6$H$_4$—CO—) with functional groups which allow for the introduction of a bridge. Some examples are disulfides, disulfide mimetics such as the —(CH2)$_n$-carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:1); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:2); Transportan GWTLN-SAGYLLGKINLKALAALAKKIL (SEQ ID NO:3); KALAWEAKLAKALAKALAKHLAKALAKALKCEA (SEQ ID NO:4); and RQIKIWFQNRRMKWKK (SEQ ID NO:5). Exemplary PTDs include, but are not limited to, YGRKKRRQRRR (SEQ ID NO:1), RKKRRQRRR (SEQ ID NO:6); an arginine homopolymer of from 3 arginine residues to 50 arginine residues; exemplary PTD domain amino acid sequences include, but are not limited to, any of the following: YGRKKRRQRRR (SEQ ID NO:1); RKKRRQRR (SEQ ID NO:7); YARAAARQARA (SEQ ID NO:8); THRLPRRRRRR (SEQ ID NO:9); and GGRRARRRRR (SEQ ID NO:10).

The carboxyl group COR$_3$ of the amino acid at the C-terminal end of an IL-10 polypeptide can be present in a free form (R3=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C1-C6-alkyl alcohols, e.g., ethyl alcohol or tert-butanol. The carboxyl group can also be amidated with primary or secondary amines such as ammonia, branched or unbranched C1-C6-alkylamines or C1-C6 di-alkylamines, e.g., methylamine or dimethylamine.

The amino group of the amino acid NR1R2 at the N-terminus of an IL-10 polypeptide can be present in a free form (R1=H and R2=H) or in the form of a physiologically-tolerated salt such as, e.g., a chloride or acetate. The amino group can also be acetylated with acids such that R1=H and R2=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which R$_1$ and/or R$_2$=C$_1$-C$_6$ alkyl or C$_2$-C$_8$ alkenyl or C$_7$-C$_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation: The clinical effectiveness of protein therapeutics is often limited by short plasma half-life and susceptibility to protease degradation. Studies of various therapeutic proteins (e.g., filgrastim) have shown that such difficulties can be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself can enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography can be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114; and Miron and Wilcheck (1993) Bio-conjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on certain molecules (e.g., IFNα) has been shown to be a hydrolytically unstable imidazolecarbamate linkage (see, e.g., Lee and McNemar, U.S. Pat. No. 5,985,263). Second generation pegylation technology has been designed to avoid these unstable linkages as well as the lack of selectivity in residue reactivity. Use of a PEG-aldehyde linker targets a single site on the N-terminus of a polypeptide through reductive amination.

PEG can be bound to a polypeptide of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide. Another activated polyethylene glycol which can be bound to a free amino group is 2,4-bis(O-methoxypolyethyleneglycol)-6-chloro-s-triazine, which can be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation: For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides can also exhibit enhanced stability or can improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide can be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type can be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, can confer acidic properties to the glycoprotein. A particular embodiment of the present disclosure comprises the generation and use of N-glycosylation variants.

The polypeptide sequences of the present disclosure can optionally be altered through changes at the nucleic acid level, particularly by mutating the nucleic acid encoding the polypeptide at preselected bases such that codons are generated that will translate into the desired amino acids.

Polysialylation: The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300 (1-2):125-30). Various techniques for site-specific polysialylation are available (see, e.g., T. Lindhout et al., PNAS 108(18)7397-7402 (2011)).

Albumin Fusion: Additional suitable components and molecules for conjugation include albumins such as human serum albumin (HSA), cyno serum albumin, and bovine serum albumin (BSA).

According to the present disclosure, albumin can be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA-drug molecule conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences.

Alternative Albumin Binding Strategies: Several albumin-binding strategies have been developed as alternatives to direct fusion and can be used with the IL-10 agents described herein. By way of example, the present disclosure contemplates albumin binding through a conjugated fatty acid chain (acylation) and fusion proteins which comprise an albumin binding domain (ABD) polypeptide sequence and the sequence of one or more of the polypeptides described herein.

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide can also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Fc-fusion Molecules: In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications: The present disclosure contemplates the use of other modifications, currently known or developed in the future, of IL-10 to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

Linkers: Linkers and their use have been described above. Any of the foregoing components and molecules used to modify the polypeptide sequences of the present disclosure can optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules can also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-serine polymers (for example, $(GS)_n$, $GSGGS_n$ (SEQ ID NO:11) and $GGGS_n$ (SEQ ID NO:12), where n is an integer of at least one), glycine-alanine polymers, alanine-serine polymers, and other flexible linkers. Glycine and glycine-serine polymers are relatively unstructured, and therefore can serve as a neutral tether between components.

Further examples of flexible linkers include glycine polymers $(G)_n$, glycine-alanine polymers, alanine-serine polymers, glycine-serine polymers (for example, $(G_mS_o)_n$, $(GSGGS)_n$ (SEQ ID NO:13), $(G_mS_oG_m)_n$ (SEQ ID NO:14), $(G_mS_oG_mS_oG_m)_n$ (SEQ ID NO:15), $(GSGGS_m)_n$ (SEQ ID NO:16), $(GSGS_mG)_n$ (SEQ ID NO:17) and $(GGGS_m)_n$ (SEQ ID NO:18), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Examples of flexible linkers include, but are not limited to GGSG (SEQ ID NO:19), GGSGG (SEQ ID NO:20), GSGSG (SEQ ID NO:21), GSGGG (SEQ ID NO:22), GGGSG (SEQ ID NO:23), and GSSSG (SEQ ID NO:24).

Additional flexible linkers include glycine polymers $(G)_n$ or glycine-serine polymers (e.g., $(GS)_n$, $(GSGGS)_n$ (SEQ ID NO:25), $(GGGS)_n$ (SEQ ID NO:26) and $(GGGGS)_n$ (SEQ ID NO:27), where n=1 to 50, for example, 1, 2, 3, 4, 5, 6, 7, 8, 9, 10, 10-20, 20-30, 30-50. Exemplary flexible linkers include, but are not limited to GGGS (SEQ ID NO:28), GGGGS (SEQ ID NO:29), GGSG (SEQ ID NO:19), GGSGG (SEQ ID NO:20), GSGSG (SEQ ID NO:21), GSGGG (SEQ ID NO:22), GGGSG (SEQ ID NO:23), and GSSSG (SEQ ID NO:24). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein. As described herein, the heterologous amino acid sequence may be a signal sequence and/or a fusion partner, such as, albumin, Fc sequence, and the like.

Therapeutic and Prophylactic Uses

In particular embodiments, the present disclosure contemplates the use of the combinations of IL-10 agents (e.g., PEG-IL-10) and immune checkpoint inhibitor(s) described herein in the treatment and/or prevention of diseases, disorders or conditions associated with cancer, a tumor, or a precancerous disease, disorder or condition. The not limiting the disclosure in any way, embodiments are contemplated wherein the IL-10 agent (and some of the immune checkpoint inhibitors described herein) reduces tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09).

The phrase "cancer-related diseases, disorders and conditions" and similar terms and phrases is meant to refer broadly to conditions that are associated, directly or indirectly, with cancer, and includes, e.g., angiogenesis and precancerous conditions such as dysplasia. While particular uses are described in detail hereafter, it is to be understood that the present disclosure is not so limited.

In accordance with the present disclosure, the combinations of an IL-10 agent and an immune checkpoint inhibitor(s) can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. In particular embodiments, the tumor or cancer is colon cancer, ovarian cancer, breast cancer, melanoma, lung cancer, glioblastoma, or leukemia.

Additional particular embodiments of the present disclosure are drawn to neoplastic (cancer-related) diseases, disorders and conditions of hematopoietic cells. Such diseases, disorders and conditions can be placed into one of two broad categories—myeloid neoplasms and lymphoid neoplasms. Each category contains different types of hematopoietic cancer with defining morphology, pathobiology, treatment, and/or prognostic features. Correct classification, along with identification of additional factors that may influence prognosis or response to chemotherapy, is essential to allow optimal treatment.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders.

Other cancers of the hematopoietic system include, but are not limited to, histiocytic and dendritic cell neoplasms.

In some embodiments, the present disclosure provides methods for treating a cancer, tumor, precancerous condition, or proliferative condition with an IL-10 agent (e.g., PEG-IL-10), an immune checkpoint inhibitor, and at least one additional therapeutic or diagnostic agent, examples of which are set forth elsewhere herein.

Pharmaceutical Compositions

The IL-10 agents and immune checkpoint inhibitors of the present disclosure can be in the form of compositions suitable for administration to a subject. In general, such compositions are "pharmaceutical compositions" comprising IL-10 and/or an immune checkpoint inhibitor(s), and one or more pharmaceutically acceptable or physiologically acceptable diluents, carriers or excipients. In certain embodiments, the IL-10 agents and immune checkpoint inhibitors are each present in a therapeutically acceptable amount. The pharmaceutical compositions can be used in the methods of the present disclosure; thus, for example, the pharmaceutical compositions can be administered ex vivo or in vivo to a subject in order to practice the therapeutic and prophylactic methods and uses described herein.

In the description of the pharmaceutical compositions, and aspects thereof, that follows, the pharmaceutical compositions are generally described in the context of an IL-10 agent. However, it is to be understood that the description also applies to the immune checkpoint inhibitor(s) of the present disclosure, either in pharmaceutical compositions comprising combinations of an IL-10 agent and an immune checkpoint inhibitor(s), or in pharmaceutical compositions comprising only one of the components (or, in the case of the immune checkpoint inhibitors, pharmaceutical compositions comprising two or more of such inhibitors).

The pharmaceutical compositions of the present disclosure can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of an IL-10 polypeptide contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver IL-10, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient can be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active ingredient of an agent co-administered with an IL-10 agent described herein is in a form suitable for oral use.

Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-10 polypeptides contemplated by the present disclosure can be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of IL-10, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, can also be utilized to release the IL-10 polypeptides disclosed herein over a defined period of time.

Particular embodiments of the present disclosure contemplate parenteral administration, and in further particular embodiments the parenteral administration is subcutaneous.

Supplementary Combination Therapy

The present disclosure contemplates the use of the combinations of IL-10 (e.g., PEG-IL-10) and an immune checkpoint inhibitor(s) in further combination with one or more active therapeutic agents or other prophylactic or therapeutic modalities (e.g., radiation). For purposes of this application, such further combinations can be referred to as "supplementary combinations", "supplementary combination therapy" and the like, and agents that are added to combinations of IL-10 and an immune checkpoint inhibitor(s) can be referred to as "supplementary agents" and the like. In such supplementary combination therapy, the various supplementary active agent(s) frequently have different mechanisms of action than IL-10 and/or the immune checkpoint inhibitor(s). Such supplementary combination therapy can be especially advantageous by allowing a dose reduction of one or more of the agents, thereby reducing or eliminating the adverse effects associated with one or more of the agents; furthermore, such supplementary combination therapy can have a synergistic therapeutic or prophylactic effect on the underlying disease, disorder, or condition. In some embodiments of the present disclosure the supplementary agent(s) is a diagnostic agent(s).

In particular embodiments, the present disclosure provides methods for treating and/or preventing diseases, disorders or conditions associated with cancer, with the IL-10 polypeptides described herein (e.g., PEG-IL-10) and an immune checkpoint inhibitor, and at least one additional therapeutic or diagnostic agent (i.e., supplementary agent(s)). In Embodiments of the present disclosure, the diseases, disorders and conditions can be cancer, tumor, or precancerous disease, disorder or condition. Although the focus of this section is on the treatment and/or prevention of diseases, disorders or conditions associated with cancer, the present disclosure contemplates the further augmentation of the supplementary combination therapy described herein with agents useful in the treatment and/or prevention of any non-cancer associated disease, disorder or condition.

In some embodiments of the present disclosure, each of the IL-10 agent (e.g., PEG-IL-10), the immune checkpoint inhibitor(s) and the supplementary agent(s) can be in a separate dosage form. By way of example, the PEG-IL-10 can be in a formulation suitable for SC administration, the immune checkpoint inhibitor can be in a formulation suitable for IV administration, and the supplementary agent can be in a formulation suitable for oral administration; in this context, each of the agents can be housed separately or two or more of the agents can be housed together (e.g., as distinct components of a kit). In other embodiments of the present disclosure, two or more of the IL-10 agent (e.g., PEG-IL-10), the immune checkpoint inhibitor(s) and the supplementary agent(s) are in the same dosage form. For example, the PEG-IL-10, the immune checkpoint inhibitor(s), and the supplementary agent(s) can be formulated for IV administration; in this context, one or more of the agents can be co-formulated (e.g., as the active therapeutic agents in a syringe).

In certain embodiments, the IL-10 agent, the immune checkpoint inhibitor(s) and the supplemental agent(s) (e.g., a chemotherapeutic agent) are administered or applied sequentially, e.g., where the IL-10 agent is administered first, an immune checkpoint inhibitor is administered second, and a supplemental agent is administered last. In other embodiments, the IL-10 agent, the immune checkpoint inhibitor(s) and the supplemental agent(s) are administered simultaneously, e.g., where two of the agents are administered simultaneously and the third is administered either before or after. Regardless of whether the IL-10 agent, the immune checkpoint inhibitor(s) and the supplemental agent(s) are administered sequentially, simultaneously, or some variation thereof, they are considered to be administered as supplementary combination therapy for purposes of the present disclosure.

The present disclosure contemplates the use of any possible dosing regimen for the supplementary combination therapy that may be acceptable, appropriate or optimal under the circumstances. The regimens described hereafter are exemplary, not exclusionary. In one embodiment, treatment with the IL-10 agent (e.g., PEG-IL-10), the immune checkpoint inhibitor(s), and the supplemental agent(s) are maintained over a period of time. In another embodiment, treatment with the IL-10 agent, the immune checkpoint inhibitor(s), and the supplemental agent(s) are reduced or continued over a period to time (e.g., when the subject is stable). In another embodiment, treatment with the supplemental agent(s) is reduced or discontinued (e.g., when the subject is stable), while treatment with the IL-10 agent and the immune checkpoint inhibitor(s) is maintained at a constant dosing regimen. In a further embodiment, treatment with the supplemental agent(s) is reduced or discontinued (e.g., when the subject is stable), treatment with the IL-10 agent is reduced (e.g., lower dose, less frequent dosing or shorter treatment regimen), and treatment with the immune checkpoint inhibitor is maintained at a constant dosing regimen. In a further embodiment, treatment with the supplemental agent(s) is reduced or discontinued (e.g., when the subject is stable), treatment with the IL-10 agent is reduced (e.g., lower dose, less frequent dosing or shorter treatment regimen), and treatment with the immune checkpoint inhibitor(s) is maintained at a constant dosing regimen.

In yet another embodiment, treatment with the supplemental agent(s) and the IL-10 agent is maintained at a constant dosing regimen, while treatment with the immune checkpoint inhibitor(s) is reduced or discontinued (e.g., when the subject is stable). In yet a further embodiment, treatment with the supplemental agent(s) and the immune checkpoint inhibitor(s) is maintained at a constant dosing regimen, while treatment with the IL-10 agent is reduced or discontinued (e.g., lower dose, less frequent dosing or shorter treatment regimen). Identification and use of other dosing regimens will be apparent to the skilled artisan.

While particular agents suitable for use with the combinations of IL-10 agents (e.g., PEG-IL-10) and immune checkpoint inhibitor(s) disclosed herein are set forth hereafter, it is to be understood that the present disclosure is not so limited. Embodiments of the present disclosure contemplate the use of supplementary agents (e.g., chemotherapeutic agents) for treating and/or preventing cancer, tumor, or precancerous or cancer-associated disease, disorder or condition.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, caliche amicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Any other agent useful in the treatment or prevention of the cancerous conditions described herein is contemplated as a supplementary agent, including, but not limited to, a cytokine or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

The present disclosure encompasses pharmaceutically acceptable salts, acids or derivatives of any of the above.

Dosing

Although the description of dosing and dosing-related topics that follows is presented in the context of IL-10, the description is largely applicable to the immune checkpoint inhibitor(s) that are used in the combination therapy disclosed herein. Specific dosing parameters pertinent to the immune checkpoint inhibitors described herein can readily be ascertained from other sources, such as package inserts that accompany finished products for sale.

The IL-10 agents (e.g., PEG-IL-10) of the present disclosure can be administered to a subject in an amount that is dependent upon, for example, the goal of the administration (e.g., the degree of resolution desired); the age, weight, sex, and health and physical condition of the subject the formulation being administered; the route of administration; and the nature of the disease, disorder, condition or symptom thereof. The dosing regimen can also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

As discussed in detail elsewhere, the present disclosure contemplates administration of IL-10 to achieve certain serum trough concentrations and/or maintain certain mean serum trough concentrations.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

In addition, an effective dose of the IL-10 agents (PEG-IL-10) of the present disclosure can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The amount of PEG-IL-10 necessary to treat a disease, disorder or condition described herein is based on the IL-10 activity of the conjugated protein, which can be determined by IL-10 activity assays known in the art. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of TNF-α or IFN-γ in biological samples.

The therapeutically effective amount of PEG-IL-10 can range from about 0.01 to about 100 µg protein/kg of body weight/day, from about 0.1 to 20 µg protein/kg of body weight/day, from about 0.5 to 10 µg protein/kg of body weight/day, or about 1 to 4 µg protein/kg of body weight/day. In some embodiments, PEG-IL-10 is administered by continuous infusion to delivery about 50 to 800 µg protein/kg of body weight/day (e.g., about 1 to 16 µg protein/kg of body weight/day of PEG-IL-10). The infusion rate can be varied based on evaluation of, for example, adverse effects and blood cell counts. Other specific dosing parameters for the IL-10 agents are described elsewhere herein.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the disclosed IL-10 polypeptide is contained in a "unit dosage form". The phrase "unit dosage form" refers to physically discrete units, each unit containing a predetermined amount of a IL-10 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-10, and pharmaceutical compositions thereof. The kits are generally in the form of a physical structure housing various components, as described below, and can be utilized, for example, in practicing the methods described above.

A kit can include one or more IL-10 agents (e.g., PEG-IL-10) disclosed herein (provided in, e.g., a sterile container), which can be in the form of a pharmaceutical composition suitable for administration to a subject. The IL-10 agents can be provided in a form that is ready for use or in a form requiring, for example, reconstitution or dilution prior to administration. When the IL-10 agents are in a form that needs to be reconstituted by a user, the kit can also include buffers, pharmaceutically acceptable excipients, and the like, packaged with or separately from the IL-10 agents. When combination therapy (e.g., an IL-10 agent and an immune checkpoint inhibitor(s) is contemplated, the kit can contain the several agents separately or they can already be combined in the kit. Similarly, when supplementary therapy (e.g., an IL-10 agent, an immune checkpoint inhibitor(s), and a supplementary agent) is contemplated, the kit can contain the several agents separately or two or more of them can already be combined in the kit. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.). Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt= nucleotide(s); pg=picogram; ng=nanogram; µg=microgram;

mg=milligram; g=gram; kg=kilogram; dl or dL=deciliter; μl or μL=microliter; ml or mL=milliliter; l or L=liter; μM=micromolar; mM=millimolar; M=molar; kDa= kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; HSA=human serum albumin; MSA=mouse serum albumin; DMEM=Dulbeco's Modification of Eagle's Medium; GC=genome copy; EDTA=ethylenediamin- etetraacetic acid.

Materials and Methods

The following general materials and methods can be used in practicing the present disclosure and/or conducting experimental work associated with various aspects of the present disclosure.

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Standard methods of histology of the immune system are described (see, e.g., Louis et al. (2002) Basic Histology: Text and Atlas, McGraw-Hill, New York, N.Y.). Depletion of immune cells (CD4+ and CD8+ T-cells) can be effected by antibody-mediated elimination. For example, 250 μg of CD4- or CD8-specific antibodies can be injected weekly, and cell depletions verified using FACS and IHC analysis.

Various mice and other animal strains can be used in conjunction with the teachings of the present disclosure. For example, immunocompetent Balb/C or B-cell-deficient Balb/C mice can be obtained from The Jackson Lab., Bar Harbor, Me. and used in accordance with standard procedures (see, e.g., Martin et al (2001) Infect. Immun., 69(11): 7067-73 and Compton et al. (2004) Comp. Med. 54(6):681-89). Other mice strains suitable for the experimental work contemplated by the present disclosure are known to the skilled artisan and are generally available from The Jackson Lab.

Serum IL-10 concentration levels and exposure levels can be determined by standard methods used in the art. For example, a serum exposure level assay can be performed by collecting whole blood (~50 μl/mouse) from mouse tail snips into plain capillary tubes, separating serum and blood cells by centrifugation, and determining IL-10 exposure levels by standard ELISA kits and techniques.

Assays to Determine the Bioactivity of Modified Forms of IL-10

The present disclosure contemplates the use of any assays and methodologies known in the art for determining the bioactivity of the IL-10 molecules described herein. The assays described hereafter are representative, and not exclusionary.

TNFα Inhibition Assay. PMA-stimulation of U937 cells (lymphoblast human cell line from lung available from Sigma-Aldrich (#85011440); St. Louis, Mo.) causes the cells to secrete TNFα, and subsequent treatment of these TNFα-secreting cells with human IL-10 causes a decrease in TNFα secretion in a dose-dependent manner. An exemplary TNFα inhibition assay can be performed using the following protocol. After culturing U937 cells in RMPI containing 10% FBS/FCS and antibiotics, plate 1×105, 90% viable U937 cells in 96-well flat bottom plates (any plasma-treated tissue culture plates (e.g., Nunc; Thermo Scientific, USA) can be used) in triplicate per condition. Plate cells to provide for the following conditions (all in at least triplicate; for 'media alone' the number of wells is doubled because one-half will be used for viability after incubation with 10 nM PMA): 5 ng/ml LPS alone; 5 ng/mL LPS+ 0.1 ng/mL rhIL-10; 5 ng/mL LPS+1 ng/mL rhIL-10; 5 ng/mL LPS+10 ng/mL rhIL-10; 5 ng/mL LPS+100 ng/mL rhIL-10; 5 ng/mL LPS+1000 ng/mL rhIL-10; 5 ng/mL LPS+0.1 ng/mL PEG-rhIL-10; 5 ng/mL LPS+1 ng/mL PEG-rhIL-10; 5 ng/mL LPS+10 ng/mL PEG-rhIL-10; 5 ng/mL LPS+100 ng/mL PEG-rhIL-10; and 5 ng/mL LPS+1000 ng/mL PEG-rhIL-10. Expose each well to 10 nM PMA in 200 μL for 24 hours, culturing at 37° C. in 5% $CO_2$ incubator, after which time ~90% of cells should be adherent. The three extra wells are re-suspended, and the cells are counted to assess viability (>90% should be viable). Wash gently but thoroughly 3× with fresh, non-PMA-containing media, ensuring that cells are still in the wells. Add 100 μL per well of media containing the appropriate concentrations (2× as the volume will be diluted by 100%) of rhIL-10 or PEG-rhIL-10, incubate at 37° C. in a 5% $CO_2$ incubator for 30 minutes. Add 100 μL per well of 10 ng/mL stock LPS to achieve a final concentration of 5 ng/mL LPS in each well, and incubate at 37° C. in a 5% $CO_2$ incubator for 18-24 hours. Remove supernatant and perform TNFα ELISA according to the manufacturer's instructions. Run each conditioned supernatant in duplicate in ELISA.

MC/9 Cell Proliferation Assay. IL-10 administration to MC/9 cells (murine cell line with characteristics of mast cells available from Cell Signaling Technology; Danvers, Mass.) causes increased cell proliferation in a dose-dependent manner. Thompson-Snipes, L. et al. ((1991) J. Exp. Med. 173:507-10) describe a standard assay protocol in which MC/9 cells are supplemented with IL3+IL10 and IL3+IL4+IL10. Vendors (e.g., R&D Systems, USA; and Cell Signaling Technology, Danvers, Mass.) use the assay as a lot release assay for rhIL10. Those of ordinary skill in the art will be able to modify the standard assay protocol described in Thompson-Snipes, L. et al, such that cells are only supplemented with IL-10.

CD8 T-cell IFNγ Secretion Assay. Activated primary human CD8 T-cells secrete IFNγ when treated with PEG-IL-10 and then with an anti-CD3 antibody. The following protocol provides an exemplary CD8 T-cell IFNγ secretion assay. Human primary peripheral blood mononuclear cells (PBMCs) can be isolated according to any standard protocol (see, e.g., Fuss et al. (2009) Current Protocols in Immunology, Unit 7.1, John Wiley, Inc., NY). 2.5 mL of PBMCs (at a cell density of 10 million cells/mL) can be cultured per well with complete RPMI, containing RPMI (Life Technologies; Carlsbad, Calif.), 10 mM HEPES (Life Technologies; Carlsbad, Calif.), 10% Fetal Calf Serum (Hyclone Thermo Fisher Scientific; Waltham, Mass.) and Penicillin/Streptomycin cocktail (Life Technologies; Carlsbad, Calif.), in any standard tissue culture treated 6-well plate (BD; Franklin Lakes, N.J.). Human pegylated-IL-10 can be added to the wells at a final concentration of 100 ng/mL; a final concentration of 10 μg/mL of antibodies blocking the function of inhibitory/checkpoint receptors can also be added in combination with pegylated-IL-10. Cells can be incubated in a humidified 37° C. incubator with 5% $CO_2$ for 6-7 days. After this incubation, CD8 T-cells can be isolated using Miltenyi Biotec's MACS cell separation technology according to the manufacture's protocol (Miltenyi Biotec; Auburn, Calif.). The isolated CD8 T-cells can then be cultured with complete RPMI containing 1 μg/mL anti-CD3 antibody (Affymetrix eBioscience; San Diego, Calif.) in any standard tissue culture plate for 4 hours. After the 4 hour incubation, the media can be collected and assayed for IFNγ using a commercial ELISA kit and following the manufacture's protocol (Affymetrix eBioscience; San Diego, Calif.).

Tumor Models and Tumor Analysis. Any art-accepted tumor model, assay, and the like can be used to evaluate the effect of the IL-10 molecules described herein on various tumors. The tumor models and tumor analyses described hereafter are representative of those that can be utilized. Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B-cell deficient Balb/C mice can be used. PEG 10-mIL-10 can be administered to the immunocompetent mice, while PEG-hIL-10 treatment can be in the B-cell deficient mice. Tumors are allowed to reach a size of 100-250 mm³ before treatment is started. IL-10, PEG-mIL-10, PEG-hIL-10, or buffer control is administered SC at a site distant from the tumor implantation. Tumor growth is typically monitored twice weekly using electronic calipers. Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C. Primary tumor growth is typically monitored twice weekly using electronic calipers. Tumor volume can be calculated using the formula (width²× length/2) where length is the longer dimension. Tumors are allowed to reach a size of 90-250 mm³ before treatment is started.

Production of Pegylated IL-10

The present disclosure contemplates the synthesis of pegylated IL-10 by any means known to the skilled artisan. The description hereafter of several alternative synthetic schemes for producing mono-PEG-IL-10 and a mix of mono-/di-PEG-IL-10 is meant to be illustrative only. While both mono-PEG-IL-10 and a mix of mono-/di-PEG-IL-10 have many comparable properties, a mix of selectively pegylated mono- and di-PEG-IL-10 improves the yield of the final pegylated product (see, e.g., U.S. Pat. No. 7,052, 686 and US Pat. Publn. No. 2011/0250163). In addition to leveraging her own skills in the production and use of PEGs (and other drug delivery technologies) suitable in the practice of the present disclosure, the skilled artisan is also familiar with many commercial suppliers of PEG-related technologies (and other drug delivery technologies). By way of example, NOF America Corp (Irvine, Calif.) supplies mono-functional Linear PEGs, bi-functional PEGs, multi-arm PESs, branched PEGs, heterofunctional PEGs, forked PEGs, and releasable PEGs; and Parchem (New Rochelle, N.Y. is a global distributor of PEG products and other specialty raw materials.

Exemplary PEG-IL-10 Synthetic Scheme No. 1. IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12K (Delmar Scientific Laboratories, Maywood, Ill.), one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate of the reaction, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

Exemplary PEG-IL-10 Synthetic Scheme No. 2. Mono-PEG-IL-10 is prepared using methoxy-PEG-aldehyde (PALD-PEG) as a linker (Inhale Therapeutic Systems Inc., Huntsville, Ala.; also available from NOF America Corp (Irvine, Calif.)). PALD-PEG can have molecular weights of 5 KDa, 12 KDa, or 20 KDa. IL-10 is dialyzed and diluted as described above, except the pH of the reaction buffer is between 6.3 and 7.5. Activated PALD-PEG linker is added to reaction buffer at a 1:1 molar ratio. Aqueous cyanoborohydride is added to the reaction mixture to a final concentration of 0.5 to 0.75 mM. The reaction is carried out at room temperature (18-25° C.) for 15-20 hours with mild agitation. The reaction is quenched with 1M glycine. Yields are analyzed by SE-HPLC. Mono-PEG-IL-10 is separated from unreacted IL-10, PEG linker and di-PEG-IL-10 by gel filtration chromatography and characterized by RP-HPLC and bioassay (e.g., stimulation of IL-10-responsive cells or cell lines).

Exemplary PEG-IL-10 Synthetic Scheme No. 3. IL-10 (e.g., rodent or primate) is dialyzed against 50 mM sodium phosphate, 100 mM sodium chloride pH ranges 5-7.4. A 1:1-1:7 molar ratio of 5K PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours. The pH of the pegylation reaction is adjusted to 6.3, 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~45-50% at termination. The reaction can be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of treating cancer in a human, comprising administering to the human:
   a) a therapeutically effective amount of an inhibitor of at least one immune checkpoint, wherein the immune checkpoint inhibitor is an anti-PD-1 or anti-PD-L1 antibody, wherein the anti-PD-1 or anti-PD-L1 antibody is selected from the group consisting of nivolumab, lambrolizumab, atezolizumab, and durvalumab; and
   b) a therapeutically effective amount of an IL-10 agent, wherein the IL-10 agent is a PEG-IL-10 agent, wherein the IL-10 component of the PEG-IL-10 agent comprises mature human IL-10, and wherein the PEG component of the PEG-IL-10 agent comprises at least one PEG molecule covalently attached to the alpha amino group of the amino acid residue at the N-terminus of IL-10, wherein the PEG component of the PEG-IL-10 agent has a molecular mass from about 5 kDa to about 20 kDa, and wherein the amount is sufficient to maintain a mean IL-10 serum trough concentration of at least 1.0 ng/mL; and
   wherein the cancer is melanoma, lung cancer, or kidney cancer.

2. The method of claim 1, wherein the cancer is lung cancer.

3. The method of claim 1, wherein the cancer is kidney cancer.

4. The method of claim 1, wherein the PEG-IL-10 agent comprises a mixture of mono-pegylated and di-pegylated IL-10.

5. The method of claim 1, wherein the administering of the inhibitor of at least one immune checkpoint and the IL-10 agent is by parenteral injection.

6. The method of claim 5, wherein the administering of the IL-10 agent is by subcutaneous injection.

7. The method of claim 1, wherein the inhibitor of at least one immune checkpoint and the IL-10 agent are administered simultaneously.

8. The method of claim 1, wherein the inhibitor of at least one immune checkpoint and the IL-10 agent are administered sequentially.

9. The method of claim 1, further comprising administering at least one additional prophylactic or therapeutic agent.

10. The method of claim 9, wherein the prophylactic or therapeutic agent is a chemotherapeutic agent.

11. A method of treating cancer in a human, comprising administering to the human:
    a) a therapeutically effective amount of an inhibitor of at least one immune checkpoint, wherein the immune checkpoint inhibitor is an anti-PD-1 or anti-PD-L1 antibody, wherein the anti-PD-1 or anti-PD-L1 antibody is selected from the group consisting of nivolumab, lambrolizumab, atezolizumab, and durvalumab; and b) a therapeutically effective amount of an IL-10 agent, wherein the IL-10 agent is a PEG-IL-10 agent, wherein the IL-10 component of the PEG-IL-10 agent comprises mature human IL-10, and wherein the PEG component of the PEG-IL-10 agent comprises at least one PEG molecule covalently attached to the alpha amino group of the amino acid residue at the N-terminus of IL-10, wherein the PEG component of the PEG-IL-10 agent has a molecular mass of about 5 kDa, and wherein the amount is sufficient to maintain a mean IL-10 serum trough concentration of at least 1.0 ng/mL; and wherein the cancer is melanoma, lung cancer, or kidney cancer.

12. The method of claim 11, wherein the cancer is lung cancer.

13. The method of claim 11, wherein the cancer is kidney cancer.

14. The method of claim 11, wherein the PEG-IL-10 agent comprises a mixture of mono-pegylated and di-pegylated IL-10.

15. The method of claim 11, wherein the administering of the inhibitor of at least one immune checkpoint and the IL-10 agent is by parenteral injection.

16. The method of claim 15, wherein the administering of the IL-10 agent is by subcutaneous injection.

17. The method of claim 11, wherein the inhibitor of at least one immune checkpoint and the IL-10 agent are administered simultaneously.

18. The method of claim 11, wherein the inhibitor of at least one immune checkpoint and the IL-10 agent are administered sequentially.

19. The method of claim 11, further comprising administering at least one additional prophylactic or therapeutic agent.

20. The method of claim 19, wherein the prophylactic or therapeutic agent is a chemotherapeutic agent.

* * * * *

SEQUENCE LISTING

```
<160> NUMBER OF SEQ ID NOS: 29

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 1

Tyr Gly Arg Lys Lys Arg Arg Gln Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 2

Arg Arg Gln Arg Arg Thr Ser Lys Leu Met Lys Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 4

Lys Ala Leu Ala Trp Glu Ala Lys Leu Ala Lys Ala Leu Ala Lys Ala
1               5                   10                  15
```

Leu Ala Lys His Leu Ala Lys Ala Leu Ala Lys Ala Leu Lys Cys Glu
            20                  25                  30

Ala

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Arg Lys Lys Arg Arg Gln Arg Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Arg Lys Lys Arg Arg Gln Arg Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Tyr Ala Arg Ala Ala Ala Arg Gln Ala Arg Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Thr His Arg Leu Pro Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 10

```
Gly Gly Arg Arg Ala Arg Arg Arg Arg Arg
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (5)..(5)
<223> OTHER INFORMATION: S at position 5 may occur n times, where n is
      an integer of at least one.

<400> SEQUENCE: 11

Gly Ser Gly Gly Ser
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (4)..(4)
<223> OTHER INFORMATION: S at position 4 may occur n times, where n is
      an integer of at least one.

<400> SEQUENCE: 12

Gly Gly Gly Ser
1

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least 1 to 20.

<400> SEQUENCE: 13

Gly Ser Gly Gly Ser
1               5

<210> SEQ ID NO 14
<211> LENGTH: 3
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(1)
<223> OTHER INFORMATION: Gly may occur m times, where m is an integer of
      at least 1 to 20.
<220> FEATURE:
<221> NAME/KEY: REPEAT
<222> LOCATION: (1)..(3)
<223> OTHER INFORMATION: Positions 1 to 3 may occur n times, where n is
      an integer of at least 1 to 20.
<220> FEATURE:
<221> NAME/KEY: REPEAT
<222> LOCATION: (2)..(2)
<223> OTHER INFORMATION: Ser may occur o times, where o is an integer of
```

```
      at least 1 to 20.
<220> FEATURE:
<221> NAME/KEY: REPEAT
<222> LOCATION: (3)..(3)
<223> OTHER INFORMATION: Gly may occur m times, where m is an integer of
      at least 1 to 20.

<400> SEQUENCE: 14

Gly Ser Gly
1

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least 1 to 20.
<220> FEATURE:
<221> NAME/KEY: REPEAT
<222> LOCATION: (1)..(1)
<223> OTHER INFORMATION: Gly may occur m times, where m is an integer of
      at least 1 to 20.
<220> FEATURE:
<221> NAME/KEY: REPEAT
<222> LOCATION: (2)..(2)
<223> OTHER INFORMATION: Ser may occur o times, where o is an integer of
      at least 1 to 20.
<220> FEATURE:
<221> NAME/KEY: REPEAT
<222> LOCATION: (3)..(3)
<223> OTHER INFORMATION: Gly may occur m times, where m is an integer of
      at least 1 to 20.
<220> FEATURE:
<221> NAME/KEY: REPEAT
<222> LOCATION: (4)..(4)
<223> OTHER INFORMATION: Ser may occur o times, where o is an integer of
      at least 1 to 20.
<220> FEATURE:
<221> NAME/KEY: REPEAT
<222> LOCATION: (5)..(5)
<223> OTHER INFORMATION: Gly may occur m times, where m is an integer of
      at least 1 to 20.

<400> SEQUENCE: 15

Gly Ser Gly Ser Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least 1 to 20.
<220> FEATURE:
<221> NAME/KEY: REPEAT
<222> LOCATION: (5)..(5)
<223> OTHER INFORMATION: Ser may occur m times, where m is an integer of
      at least 1 to 20.

<400> SEQUENCE: 16

Gly Ser Gly Gly Ser
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least 1 to 20.
<220> FEATURE:
<221> NAME/KEY: REPEAT
<222> LOCATION: (4)..(4)
<223> OTHER INFORMATION: Ser may occur m times, where m is an integer of
      at least 1 to 20.

<400> SEQUENCE: 17

Gly Ser Gly Ser Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(4)
<223> OTHER INFORMATION: Positions 1 to 4 may occur n times, where n is
      an integer of at least 1 to 20.
<220> FEATURE:
<221> NAME/KEY: REPEAT
<222> LOCATION: (4)..(4)
<223> OTHER INFORMATION: Ser may occur m times, where m is an integer of
      at least 1 to 20.

<400> SEQUENCE: 18

Gly Gly Gly Ser
1

<210> SEQ ID NO 19
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 19

Gly Gly Ser Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 20

Gly Gly Ser Gly Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide
```

```
<400> SEQUENCE: 21

Gly Ser Gly Ser Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Gly Ser Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 23

Gly Gly Gly Ser Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 24

Gly Ser Ser Ser Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer from 1 to 50.

<400> SEQUENCE: 25

Gly Ser Gly Gly Ser
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(4)
<223> OTHER INFORMATION: Positions 1 to 4 may occur n times, where n is
      an integer from 1 to 50.

<400> SEQUENCE: 26

Gly Gly Gly Ser
1
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer from 1 to 50.

<400> SEQUENCE: 27

Gly Gly Gly Gly Ser
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 28

Gly Gly Gly Ser
1

<210> SEQ ID NO 29
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 29

Gly Gly Gly Gly Ser
1               5
```